United States Patent
Malamas et al.

(10) Patent No.: US 7,700,606 B2
(45) Date of Patent: *Apr. 20, 2010

(54) IMIDAZOLE AMINES AS INHIBITORS OF β-SECRETASE

(75) Inventors: Michael Sotirios Malamas, Jamison, PA (US); Keith Douglas Barnes, Rexford, NY (US); Matthew Robert Johnson, Guilderland, NY (US)

(73) Assignee: Wyeth LLC, Madison, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 11/893,485

(22) Filed: Aug. 16, 2007

(65) Prior Publication Data

US 2008/0051390 A1    Feb. 28, 2008

Related U.S. Application Data

(60) Provisional application No. 60/838,357, filed on Aug. 17, 2006.

(51) Int. Cl.
C07D 487/04 (2006.01)
A61K 31/519 (2006.01)

(52) U.S. Cl. ............... 514/259.1; 544/230; 544/281

(58) Field of Classification Search .......... 544/230, 544/281; 514/259.1
See application file for complete search history.

(56) References Cited

U.S. PATENT DOCUMENTS

| | | | |
|---|---|---|---|
| 4,140,793 | A | 2/1979 | Ward |
| 4,225,613 | A | 9/1980 | Ward |
| 6,054,457 | A | 4/2000 | Setoi et al. |
| 6,399,824 | B1 | 6/2002 | Hofmeister et al. |
| 6,656,957 | B1 | 12/2003 | Allgeier et al. |
| 6,689,804 | B2 | 2/2004 | Wu et al. |
| 6,974,829 | B2 | 12/2005 | Tung et al. |
| 7,285,682 | B2 | 10/2007 | Hu |
| 2005/0282825 | A1 | 12/2005 | Malamas et al. |
| 2005/0282826 | A1 | 12/2005 | Malamas et al. |
| 2006/0111370 | A1 | 5/2006 | Zhu et al. |
| 2006/0160828 | A1 | 7/2006 | Malamas et al. |
| 2006/0173049 | A1 | 8/2006 | Malamas et al. |
| 2006/0183790 | A1 | 8/2006 | Cole et al. |
| 2006/0183792 | A1 | 8/2006 | Fobare et al. |
| 2007/0004730 | A1 | 1/2007 | Zhou |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0191431 | A1 | 8/2007 | Zhou |
| 2007/0203116 | A1 | 8/2007 | Quagliato et al. |
| 2008/0051390 | A1 | 2/2008 | Malamas et al. |

FOREIGN PATENT DOCUMENTS

| | | |
|---|---|---|
| EP | 0861831 A1 | 9/1998 |
| GB | 2013192 A | 8/1979 |
| WO | WO 97/45417 A1 | 12/1997 |
| WO | WO 98/45267 | 10/1998 |
| WO | WO 01/87829 A1 | 11/2001 |
| WO | WO 03/053938 A1 | 7/2003 |
| WO | WO 03/064396 A1 | 8/2003 |
| WO | WO 03/094854 A2 | 11/2003 |
| WO | WO 2004/058727 A1 | 7/2004 |
| WO | WO 2005/005412 A1 | 1/2005 |
| WO | WO 2005/058311 A1 | 6/2005 |
| WO | WO 2006/009653 A1 | 1/2006 |
| WO | WO 2006/065277 A2 | 6/2006 |
| WO | WO 2007/005404 A1 | 1/2007 |
| WO | WO 2007/016012 A2 | 2/2007 |

OTHER PUBLICATIONS

Li et al. (PNAS, Mar. 9, 2004, vol. 101, No. 10, pp. 3632-3637).*
PCT Preliminary Report on Patentability, Written Opinion of the ISR, International Patent Application PCT/US2007/075690, International filing date Aug. 10, 2007.
Abbott et al., Molecular Medicine Today, 1996, vol. 2, p. 106-113.
Allimony et al., "Synthesis and antimicrobial activity of some nitrogen heterobicyclic systems: Part I", Indian Journal of Chemistry, 1999, vol. 38B, pp. 445-451.
Fact Sheet Alzheimer's Association, 2006.
Lefrance-Jullien et al., "Design and charaterization of a new cell-permeant inhibitor of the beta-secretase BACE1", British Journal of Pharmacology, 2005, vol. 145, pp. 228-235.
Lyketsos et al., "Position statement of the American Association for Geriatric Psychiatry regarding principles of care for patients with dementia resulting from Alzheimer's Disease", 2006 vol. 14, pp. 561-573.
Alzheimer's Disease, retrieved from Internet on Jun. 27, 2007, http://www.mayoclinic.com/health/alzheimers-disease/DA00161/DSECTION-3.

(Continued)

Primary Examiner—Kahsay T Habte
(74) Attorney, Agent, or Firm—Ram W. Sabnis

(57) ABSTRACT

The present invention provides a compound of formula I and the use thereof for the therapeutic treatment, prevention or amelioration of a disease or disorder characterized by elevated β-amyloid deposits or β-amyloid levels in a patient.

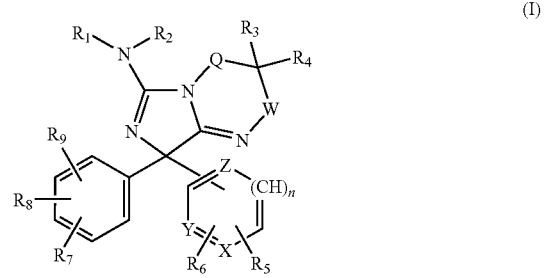

(I)

18 Claims, No Drawings

OTHER PUBLICATIONS

National Institute of Neurological Discorders and Stroke, "Alzheimer's Disease Information Page", retrieved from internet on Jun. 27, 2007, http://www.ninds.nih.gov/disorders/alzheimersdisease/alzheimersdisease.htm.

PCT Preliminary Report on Patentability, Written Opinion of the ISR, International Patent Application PCT/US2006/024793, International filing date Jun. 26, 2006.

PCT Preliminary Report on Patentability, Written Opinion of the ISR, International Patent Application PCT/US2006/024912, International filing date Jun. 26, 2006.

Selkoe, "Alzheimer's Disease: Genes, Proteins, and Therapy", Physiological Reviews, 2001, vol. 81(2), pp. 741-766.

Su et al. "Drug delivery across the blood-brain barrier: why is it difficult? How to measure and improve it?", Expert Opinion on Drug Delivery, Abstract, 2006, vol. 3, pp. 419-425.

Tao et al., "Synthesis of Conformationally constrained spirohydantoins with a Dibenzo[a,d]heptadiene ring", Synthesis 2000, No. 10, pp. 1449-1453.

Vandana et al., "Transferring coupled liposomes as drug delivery carriers for brain trageting of 5-florouracil", Journal of Drug Targeting, Abstract, 2005, vol. 13 pp. 245-250.

Varghese et al., "Human beta-secretase (BACE) and BACE Inhibitors", J. Med. Chem. 2003, vol. 46(22), pp. 4625-4630.

Xiao et al., "An improved procedure for the synthesis of 4,4-disubstituted-3-oxo-1,2,5-thiadiazolidine 1,1-dioxides", J. Heterocyclic Chem., 2000, vol. 37, pp. 773-777.

Yamada et al., "Hydantoin derivatives, I. Actions on central nervous system of 5,5-diarylhydantoins and 5,5-diarylhydantion-2-imines", Abstract, Oyo Yakuri, 1975, vol. 9(6), pp. 841-847.

* cited by examiner

IMIDAZOLE AMINES AS INHIBITORS OF β-SECRETASE

This application claims the benefit under 35 U.S.C. §119 (e) to co-pending U.S. provisional application No. 60/838357, filed Aug. 17, 2006, which is hereby incorporated by reference in its entirety.

BACKGROUND OF THE INVENTION

Alzheimer's disease (AD), a progressive degenerative disease of the brain primarily associated with aging, is a serious healthcare problem. Clinically, AD is characterized by the of loss of memory, cognition, reasoning, judgment, and orientation. Also affected, as the disease progresses, are motor, sensory, and linguistic abilities until global impairment of multiple cognitive functions occurs. These cognitive losses take place gradually, but typically lead to severe impairment and eventual death in 4-12 years. Patients with AD display characteristic β-amyloid deposits in the brain and in cerebral blood vessels (β-amyloid angiopathy) as well as neurofibrillary tangles. Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other dementia-inducing disorders.

The family of proteins known as β-amyloid are thought to be causal for the pathology and subsequent cognitive decline in Alzheimer's disease. Proteolytic processing of the amyloid precursor protein (APP) generates amyloid β (A-beta) peptide; specifically, A-beta is produced by the cleavage of APP at the N-terminus by β-secretase and at the C-terminus by one or more γ-secretases. Aspartyl protease enzyme, or β-secretase enzyme (BACE), activity is correlated directly to the generation of A-beta peptide from APP (Sinha, et al, *Nature*, 1999, 402, 537-540). Increasingly, studies indicate that the inhibition of the β-secretase enzyme, inhibits the production of A-beta peptide. The inhibition of β-secretase and consequent lowering of A-beta peptide may lead to the reduction of β-amyloid deposits in the brain and β-amyloid levels in the cerebral blood vessels and to an effective treatment of a disease or disorder caused thereby.

Therefore, it is an object of this invention to provide compounds which are inhibitors of β-secretase and are useful as therapeutic agents in the treatment, prevention or amelioration of a disease or disorder characterized by elevated β-amyloid deposits or β-amyloid levels in a patient.

It is another object of this invention to provide therapeutic methods and pharmaceutical compositions useful for the treatment, prevention or amelioration of a disease or disorder characterized by elevated β-amyloid deposits or β-amyloid levels in a patient.

It is a feature of this invention that the compounds provided may also be useful to further study and elucidate the β-secretase enzyme.

These and other objects and features of the invention will become more apparent by the detailed description set forth hereinbelow.

SUMMARY OF THE INVENTION

The present invention provides an imidazole amine of formula I

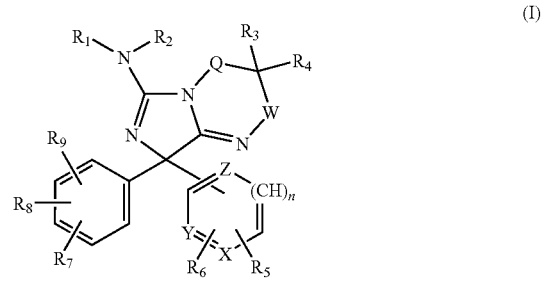

wherein
Q is O, S or CH$_2$;
W is O, S or CH$_2$;
X is N, NO, SO$_m$, O or CH;
Y is N, NO, SO$_m$, O or CR$_{10}$;
Z is N, NO, SO$_m$, O or CR$_{11}$ with the proviso that when X is CH, Y is CR$_{10}$ and Z is CR$_{11}$ then one of Q or W must be O or S;
m is 0, 1 or 2;
n is 0 or 1;
R$_1$ and R$_2$ are each independently H or an optionally substituted C$_1$-C$_4$alkyl group;
R$_3$ and R$_4$ are each independently H, or an optionally substituted C$_1$-C$_4$ alkyl group or R$_3$ and R$_4$ may be taken together to form a 4- to 7-membered ring optionally containing one or two heteroatoms selected from O, N or S;
R$_5$ and R$_6$ are each independently H, halogen, NO$_2$, CN, OR$_{12}$, CO$_2$R$_{13}$, COR$_{14}$, NR$_{17}$R$_{18}$, SO$_p$NR$_{19}$R$_{20}$ or a C$_1$-C$_6$alkyl, C$_1$-C$_6$haloalkyl, C$_2$-C$_6$alkenyl, C$_2$-C$_6$alkynyl or C$_3$-C$_8$cycloalkyl group each optionally substituted;
R$_7$ and R$_8$ are each independently H, halogen, NO$_2$, CN, OR$_{15}$, NR$_{17}$R$_{18}$ or a C$_1$-C$_6$alkyl, C$_1$-C$_6$haloalkyl, C$_2$-C$_6$alkenyl, C$_2$-C$_6$alkynyl, C$_3$-C$_8$cycloalkyl or cycloheteroalkyl group each optionally substituted or when attached to adjacent carbon atoms R$_7$ and R$_8$ may be taken together with the atoms to which they are attached to form an optionally substituted 5- to 7-membered ring optionally containing one or two heteroatoms selected from O, N or S;
R$_9$ is H, halogen, NO$_2$, CN, OR$_{15}$, NR$_{17}$R$_{18}$ or a C$_1$-C$_6$alkyl, C$_1$-C$_6$haloalkyl, C$_2$-C$_6$alkenyl, C$_2$-C$_6$alkynyl, C$_3$-C$_8$cycloalkyl, cycloheteroalkyl, aryl or heteroaryl group each optionally substituted;
R$_{10}$ and R$_{11}$ are each independently H or a C$_1$-C$_6$alkyl, C$_1$-C$_6$haloalkyl, C$_2$-C$_6$alkenyl, C$_2$-C$_6$alkynyl, C$_3$-C$_8$cycloalkyl, cycloheteroalkyl or aryl group each optionally substituted;
R$_{12}$, R$_{13}$, R$_{14}$ and R$_{15}$ are each independently H or a C$_1$-C$_6$alkyl, C$_1$-C$_6$haloalkyl, C$_2$-C$_6$alkenyl, C$_2$-C$_6$alkynyl, C$_3$-C$_8$cycloalkyl, cycloheteroalkyl, aryl or heteroaryl group each optionally substituted;
R$_{17}$, R$_{18}$, R$_{19}$ and R$_{20}$ are each independently H, C$_1$-C$_4$alkyl, C$_3$-C$_8$cycloalkyl or R$_{17}$ and R$_{18}$ or R$_{19}$ and R$_{20}$ may be taken together with the atom to which they are attached to form a 5- to 7-membered ring optionally containing an additional heteroatom selected from O, N or S; and
p is 0, 1 or 2; or
a tautomer thereof, a stereoisomer thereof or a pharmaceutically acceptable salt thereof.

The present invention also provides therapeutic methods and pharmaceutical compositions useful for the treatment, prevention or amelioration of a disease or disorder characterized by increased β-amyloid deposits or increased β-amyloid levels in a patient.

DETAILED DESCRIPTION OF THE INVENTION

Alzheimer's disease (AD) is a major degenerative disease of the brain which presents clinically by progressive loss of memory, cognition, reasoning, judgement and emotional stability and gradually leads to profound mental deteoriation and death. The exact cause of AD is unknown, but increasing evidence indicates that amyloid beta peptide (A-beta) plays a central role in the pathogenesis of the disease. (D. B. Schenk; R. E. Rydel et al, Journal of Medicinal Chemistry, 1995, 21,4141 and D. J. Selkoe, Physiology Review, 2001, 81, 741). Patients with AD exhibit characteristic neuropathological markers such as neuritic plaques (and in β-amyloid angiopathy, deposits in cerebral blood vessels) as well as neurofibrillary tangles detected in the brain at autopsy. A-beta is a major component of neuritic plaques in AD brains. In addition, β-amyloid deposits and vascular β-amyloid angiopathy also characterize individuals with Downs Syndrome, Hereditary Cerebral Hemmorhage with Amyloidosis of the Dutch type and other neurodegenreative and dementia-inducing disorders. Over expression of the amyloid precursor protein (APP), altered cleavage of APP to A-beta or a decrease in the clearance of A-beta from a patient's brain may increase the levels of soluble or fibrullar forms of A-beta in the brain. The β-site APP cleaving enzyme, BACE1, also called memapsin-2 or Asp-2, was identified in 1999 (R. Vassar, B. D. Bennett, et al, Nature, 1999, 402, 537). BACE1 is a membrane-bound aspartic protease with all the known functional properties and characteristics of β-secretase. Parallel to BACE1, a second homologous aspartyl protease named BACE2 was found to have β-secretase activity in vitro. Low molecular weight, non-peptide, non-substrate-related inhibitors of BACE1 or β-secretase are earnestly sought both as an aid in the study of the β-secretase enzyme and as potential therapeutic agents.

Surprisingly, it has now been found that imidazole amine compounds of formula I demonstrate inhibition of β-secretase and the selective inhibition of BACE1. Advantageously, said imidazole amine compounds may be used as effective therapeutic agents for the treatment, prevention or amelioration of a disease or disorder characterized by elevated β-amyloid deposits or β-amyloid levels in a patient. Accordingly, the present invention provides an imidazole amine compound of formula I

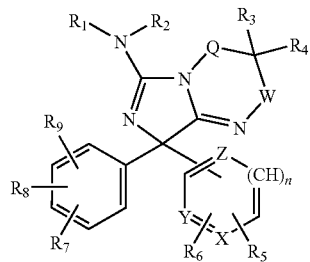

(I)

wherein
Q is O, S or $CH_2$;
W is O, S or $CH_2$;
X is N, NO, $SO_m$, O or CH;
Y is N, NO, $SO_m$, O or $CR_{10}$;
Z is N, NO, $SO_m$, O or $CR_{11}$ with the proviso that when X is CH, Y is $CR_{10}$ and Z is $CR_{11}$ then one of Q or W must be O or S;
m is 0, 1 or 2;
n is 0 or 1;
$R_1$ and $R_2$ are each independently H or an optionally substituted $C_1$-$C_4$alkyl group;
$R_3$ and $R_4$ are each independently H, or an optionally substituted $C_1$-$C_4$ alkyl group or $R_3$ and $R_4$ may be taken together to form a 4- to 7-membered ring optionally containing one or two heteroatoms selected from O, N or S;
$R_5$ and $R_6$ are each independently H, halogen, $NO_2$, CN, $OR_{12}$, $CO_2R_{13}$, $COR_{14}$, $NR_{17}R_{18}$, $SO_pNR_{19}R_{20}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted;
$R_7$ and $R_8$ are each independently H, halogen, $NO_2$, CN, $OR_{15}$, $NR_{17}R_{18}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or cycloheteroalkyl group each optionally substituted or when attached to adjacent carbon atoms $R_7$ and $R_8$ may be taken together with the atoms to which they are attached to form an optionally substituted 5- to 7-membered ring optionally containing one or two heteroatoms selected from O, N or S;
$R_9$ is H, halogen, $NO_2$, CN, $OR_{15}$, $NR_{17}R_{18}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted;
$R_{10}$ and $R_{11}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl or aryl group each optionally substituted;
$R_{12}$, $R_{13}$, $R_{14}$ and $R_{15}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted;
$R_{17}$, $R_{18}$, $R_{19}$ and $R_{20}$ are each independently H, $C_1$-$C_4$alkyl, $C_3$-$C_8$cycloalkyl or $R_{17}$ and $R_{18}$ or $R_{19}$ and $R_{20}$ may be taken together with the atom to which they are attached to form a 5- to 7-membered ring optionally containing an additional heteroatom selected from O, N or S; and
p is 0, 1 or 2; or a tautomer thereof, a stereoisomer thereof or a pharmaceutically acceptable salt thereof.

As used in the specification and claims, the term halogen designates F, Cl, Br or I and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein $X_1$ is NR, O or S; and R is H or an optional substituent as described hereinbelow:

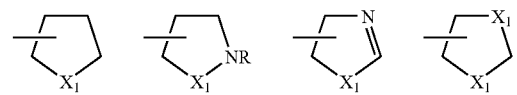

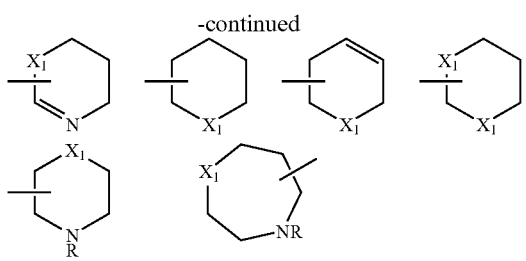

Similarly, as used in the specification and claims, the term heteroaryl designates a five- to ten-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolyl, benzothienyl, benzofuranyl, benzisoxazolyl or the like. The term aryl designates a carbocyclic aromatic ring system such as phenyl, naphthyl, anthracenyl or the like. The term aryl $(C_1-C_4)$alkyl designates an aryl group as defined hereinabove attached to a $C_1-C_4$alkyl group which may be straight or branched. Said aryl$(C_1-C_4)$alkyl groups include benzyl, phenethyl, napthtylmethyl, or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different. Preferably the term haloalkyl designates $CF_3$ and the term haloalkoxy designates $OCF_3$.

In the specification and claims, when the terms $C_1-C_6$alkyl, $C_2-C_6$alkenyl, $C_2-C_6$alkynyl, $C_3-C_8$cycloalkyl, cycloheteroalkyl, aryl, aryl$(C_1-C_4)$alkyl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more tautomers. One skilled in the art will recognize that compounds of formula I may also exist as the tautomer It as shown below.

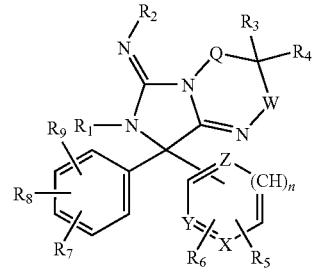

(It)

Tautomers often exist in equilibrium with each other. As these tautomers interconvert under environmental and physiological conditions, they provide the same useful biological effects. The present invention includes mixtures of such tautomers as well as the individual tautomers of Formula I and Formula It.

The compounds of the invention may contain one or more asymmetric carbon atoms or one or more asymmetric (chiral) centers and may thus give rise to optical isomers and diastereomers. Thus, the invention includes such optical isomers and disastereomers; as well as the racemic and resolved, enantiomerically pure stereoisomers; as well as other mixtures of the R and S stereoisomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof, the tautomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein $R_1$ and $R_2$ are H. Another group of preferred compounds of the invention are those compounds of formula I wherein $R_9$ is an optionally substituted heteroaryl group. Also preferred are those formula I compounds wherein X is N. A further group of preferred compounds of the invention are those compounds of formula I wherein $R_9$ is an optionally substituted heteroaryl group and is attached to the phenyl ring in the 3-position of the phenyl ring.

More preferred compounds of the invention are those compounds of formula I wherein $R_1$ and $R_2$ are H and $R_9$ is an optionally substituted heteroaryl group. Another group of more preferred compounds of the invention are those compounds of formula I wherein $R_1$ and $R_2$ are H; $R_9$ is an optionally substituted heteroaryl group; and X is N. A further group of more preferred compounds of the invention are those compounds of formula I wherein $R_1$ and $R_2$ are H and $R_9$ is an optionally substituted heteroaryl group and is attached to the phenyl ring in the 3-position of the phenyl ring.

Preferred compounds of formula I include:

8-[3-(2-fluoropyridin-3-yl)-phenyl]-8-pyridin-4-yl-2,3,4,8-tetrahydroimidazo[1,5-a]pyrimidin-6-amine;

8-(2,6-diethylpyridin-4-yl)-8-[3-(2-fluoropyridin-3-yl)-phenyl]-2,3,4,8-tetrahydro-imidazo[1,5-a]pyrimidin-6-amine;

8-(1-ethyl-1H-pyrazol-4-yl)-8-[3-(2-fluoropyridin-3-yl)phenyl]-2,3,4,8-tetrahydro-imidazo[1,5-a]pyrimidin-6-amine;

8-[3-(2-fluoropyridin-3-yl)phenyl]-8-[1-(2,2,2-trifluoroethyl)-1H-pyrazol-4-yl]-2,3,4,8-tetrahydroimidazo[1,5-a]pyrimidin-6-amine;

8-[3-(2-fluoropyridin-3-yl)phenyl]-8-[4-(trifluoromethoxy)phenyl]-3,4-dihydro-8H-imidazo[5,1-c][1,2,4]oxadiazin-6-amine;

8-[3-(5-fluoropyridin-3-yl)phenyl]-8-[4-(trifluoromethoxy)phenyl]-3,4-dihydro-8H-imidazo[5,1-c][1,2,4]oxadiazin-6-amine;

the tautomers thereof; the stereoisomers thereof; or the pharmaceutically acceptable salts thereof.

Advantageously, the present invention provides a process for the preparation of a compound of formula I wherein $R_9$ is an optionally substituted aryl or heteroaryl group (Ia) which comprises reacting a compound of formula II wherein Hal is Cl or Br with an optionally substituted aryl or heteroaryl group having a leaving group selected from $B(OH)_2$, $Sn(Bu)_3$ or $Sn(CH_3)_3$ in the presence of a palladium catalyst and an inorganic base optionally in the presence of a solvent. The process is shown in flow diagram I, wherein A represents an optionally substituted aryl or heteroaryl group; W is $B(OH)_2$, $Sn(Bu)_3$ or $Sn(CH_3)_3$; and Hal is Cl or Br.

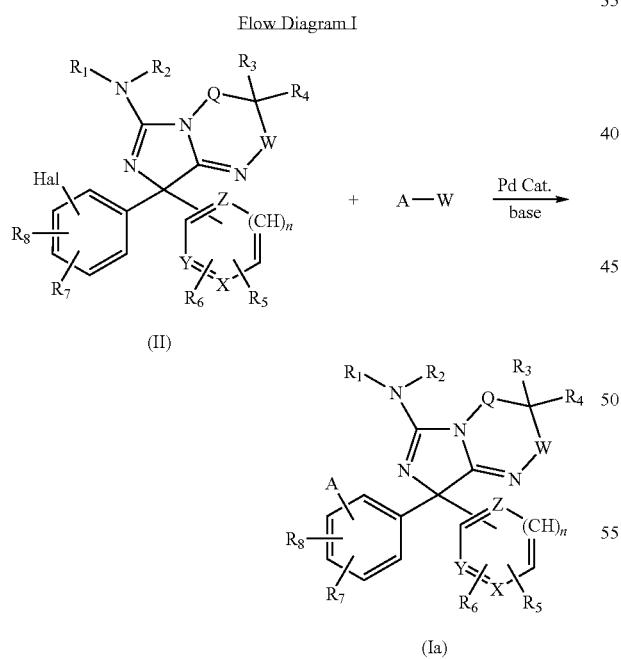

Palladium catalysts suitable for use in the process of the invention include Pd(0) or Pd(II) catalysts such as dichlorobis(tri-o-tolylphosphine)palladium(II), $Pd(OCOCH_3)_2$/tri-o-tolylphosphine, tetrakis(triphenylphosphine)palladium(0), tris(dibenzylideneacetone)dipalladium(0)triphenylphosphine, or the like.

Inorganic bases suitable for use in the inventive process include Na or K hydroxides, carbonates or bicarbonates, preferably $Na_2CO_3$ or $K_2CO_3$.

Solvents suitable for use in the inventive process include polar or non-polar organic solvents such as toluene, diethoxy ethyl ether, dioxane, ethyleneglycol dimethyl ether or any non-reactive organic solvent which is capable of solubilizing the formula II or heteroaryl compounds.

Compounds of formula II may be prepared using conventional synthetic methods and, if required, standard separation or isolation techniques. For example, compounds of formula II wherein $R_1$ and $R_2$ are H and Q and W are $CH_2$ (IIa), may be prepared by reacting a compound of formula III with a diamine of formula IV to give the bicyclic compound of formula V and reacting said formula V compound with t-butyl hydroperoxide and ammonium hydroxide to give the desired formula IIa compound. The reaction is shown in flow diagram II wherein Hal is Cl or Br.

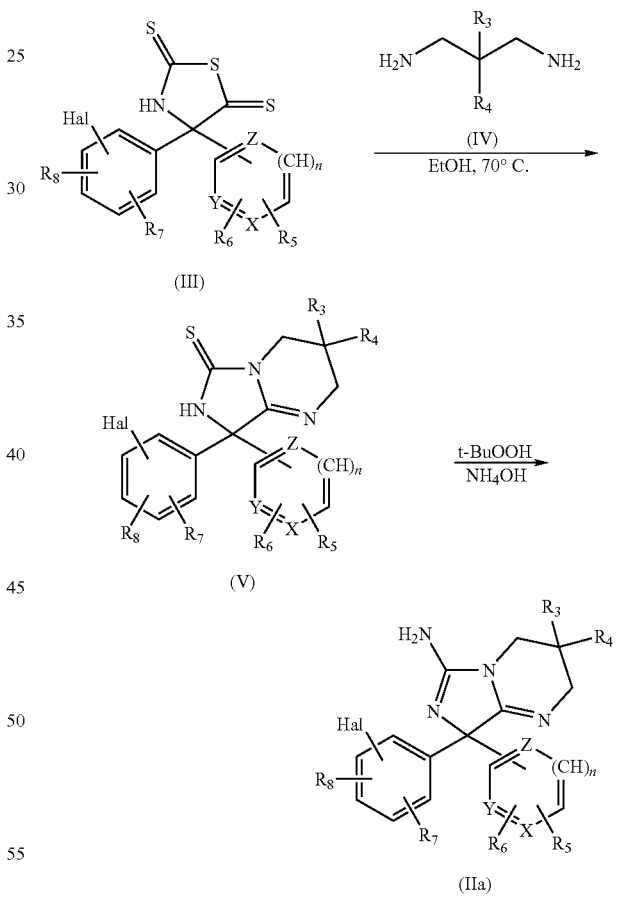

Similarly, compounds of formula II wherein $R_1$ and $R_2$ are H; $R_3$ and $R_4$ are H; Q is $CH_2$; and W is O (IIb) may be prepared by reacting the formula III compound with 2-(aminooxy)ethanamine dihydrochloride in the presence of a base such as triethylamine and a solvent to give the bicyclic compound of formula VI and reacting said formula VI compound with t-butyl hydroperoxide and ammonium hydroxide to give the desired formula IIb compound. The reaction is shown in flow diagram III wherein Hal is Cl or Br.

Flow Diagram III

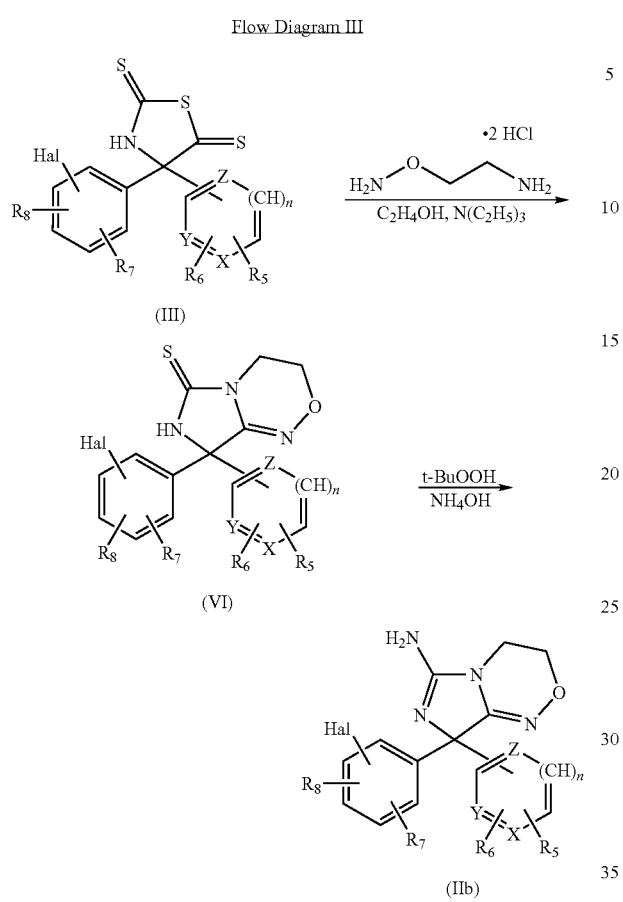

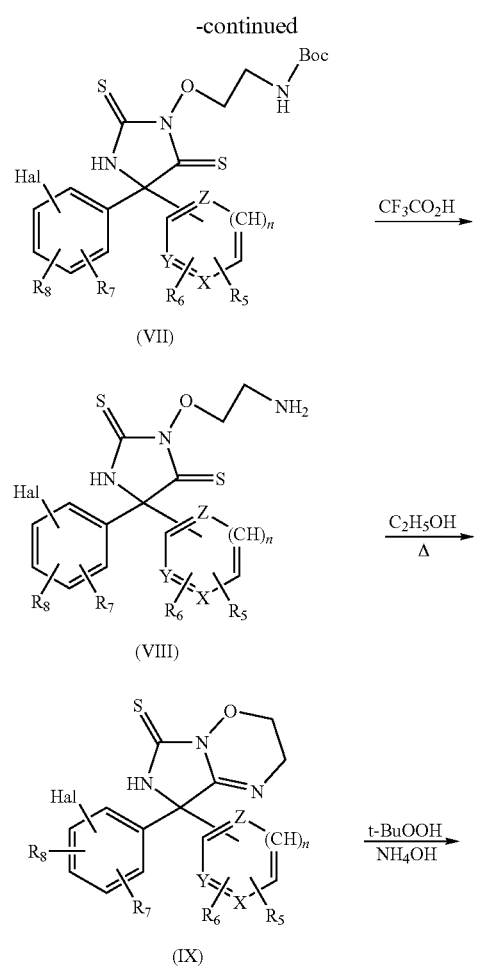

Compounds of formula II wherein $R_1$ and $R_2$ are H; $R_3$ and $R_4$ are H; Q is O; and W is $CH_2$ (IIc) may be prepared by reacting the formula III compound with Boc-protected 2-(aminooxy)ethanamine give the protected amine compound of formula VII; deprotecting said formula VII compound in the presence of an acid such as trifluoroacetic acid to give the corresponding free amine of formula VIII; and cyclizing the formula VIII compound to give the bicyclic compound of formula IX and reacting said formula IX compound with t-butyl hydroperoxide and ammonium hydroxide to give the desired formula IIc compound. The reaction is shown in flow diagram IV wherein Boc is t-butylcarbonyloxy and Hal is Cl or Br.

Flow Diagram IV

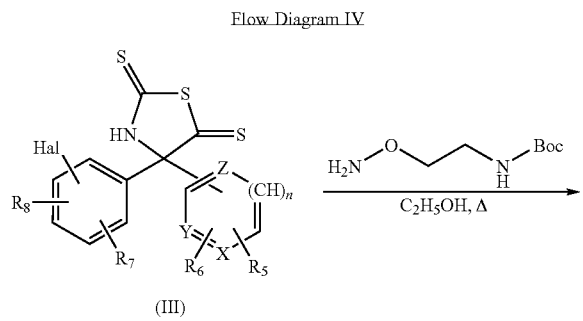

Compounds of formula IIa, IIb and IIc may be converted to the corresponding compounds of formula Ia wherein $R_1$ and $R_2$ are H using the procedure described hereinabove in flow diagram I.

Compounds of formula III may be readily prepared by reacting a heteroaryl halide compound of formula X with a benzonitrile compound of formula XI in the presence of a base such as t-butyl lithium to give the methylamine of formula XII: reacting said formula XII amine with thiophosgene in the presence of a base such as $NaHCO_3$ to give the thiocyanate compound of formula XIII; and reacting said formula XIII thiocyanate with carbon disulfide in the presence of a base such as potassium t-butoxide to give the desired compound of formula III. The reaction is shown in flow diagram V wherein Hal represents Cl or Br.

FLOW DIAGRAM V

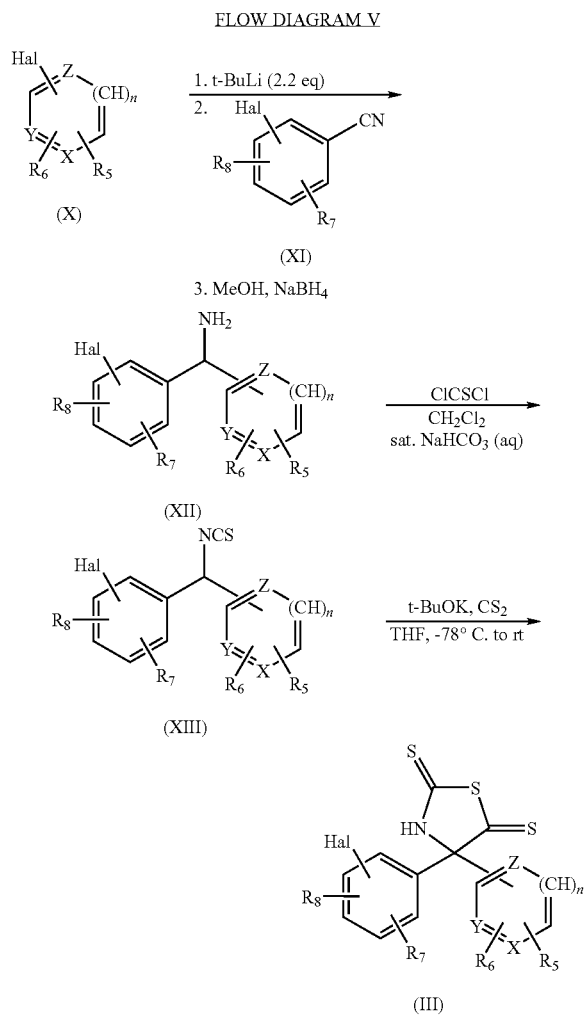

Compounds of formula I wherein $R_9$ is other than an optionally substituted aryl or heteroaryl group may be prepared by the reactions shown hereinabove in flow diagrams II through IV and employing the corresponding formula III compound wherein Hal is replaced by the desired $R_9$ substituent.

Compounds of formula I wherein $R_1$ and $R_2$ are other than H may be prepared using standard alkylation techniques such as reacting the compound of formula I wherein $R_1$ and $R_2$ are H with an alkyl halide, $R_1$-Hal, to give the compound of formula I wherein $R_2$ is H (Id) and optionally reacting said formula Id compound with a second alkyl halide, $R_2$-Hal, to give the desired formula I compound wherein $R_1$ and $R_2$ are other than H.

Advantageously, the compounds of the invention are useful for the treatment, prevention or amelioration of a disease or disorder characterized by elevated β-amyloid deposits or β-amyloid levels in a patient, including Alzheimer's disease, Downs Syndrome, Hereditary Cerebral Hemorrhage with Amyloidosis of the Dutch type or other neurodegenerative or dementia-inducing disorders. Accordingly, the present invention provides a method for the treatment, prevention or amelioration of a disease or disorder characterized by elevated β-amyloid deposits or β-amyloid levels in a patient which comprises providing said patient with a therapeutically effective amount of a compound of formula I as described hereinabove. The compound may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

Alternatively, the use of sustained delivery devices may be desirable, in order to avoid the necessity for the patient to take medications on a daily basis. "Sustained delivery" is defined as delaying the release of an active agent, i.e., a compound of the invention, until after placement in a delivery environment, followed by a sustained release of the agent at a later time. Those of skill in the art know suitable sustained delivery devices. Examples of suitable sustained delivery devices include, e.g., hydrogels (see, e.g., U.S. Pat. Nos. 5,266,325; 4,959,217; and 5,292,515), an osmotic pump, such as described by Alza (U.S. Pat. Nos. 4,295,987 and 5,273,752) or Merck (European Patent No. 314,206), among others; hydrophobic membrane materials, such as ethylenemethacrylate (EMA) and ethylenevinylacetate (EVA); bioresorbable polymer systems (see, e.g., International Patent Publication No. WO 98/44964, Bioxid and Cellomeda; U.S. Pat. Nos. 5,756,127 and 5,854,388); other bioresorbable implant devices have been described as being composed of, for example, polyesters, polyanhydrides, or lactic acid/glycolic acid copolymers (see, e.g., U.S. Pat. No. 5,817,343 (Alkermes Inc.)). For use in such sustained delivery devices, the compounds of the invention may be formulated as described herein.

In another aspect, the invention provides a pharmaceutical kit for delivery of a product. Suitably, the kit contains packaging or a container with the compound formulated for the desired delivery route. For example, if the kit is designed for administration by inhalation, it may contain a suspension containing a compound of the invention formulated for aerosol or spray delivery of a predetermined dose by inhalation. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the spray pump or other delivery device.

Other suitable components to such kits will be readily apparent to one of skill in the art, taking into consideration the desired indication and the delivery route. The doses may be repeated daily, weekly, or monthly, for a predetermined length of time or as prescribed.

For a more clear understanding, and in order to illustrate the invention more clearly, specific examples thereof are set forth hereinbelow. The following examples are merely illustrative and are not to be understood as limiting the scope and underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

Unless otherwise noted, all parts are parts by weight. The term NMR designates nuclear magnetic resonance. The terms DME and DMF designate ethylene glycol dimethyl ether and dimethyl formamide, respectively.

EXAMPLE 1

Preparation of 8-[3-(2-Fluoropyridin-3-yl)phenyl]-8-pyridin-4-yl-2,3,4,8-tetrahydroimidazo[1,5-a]pyrimidin-6-amine

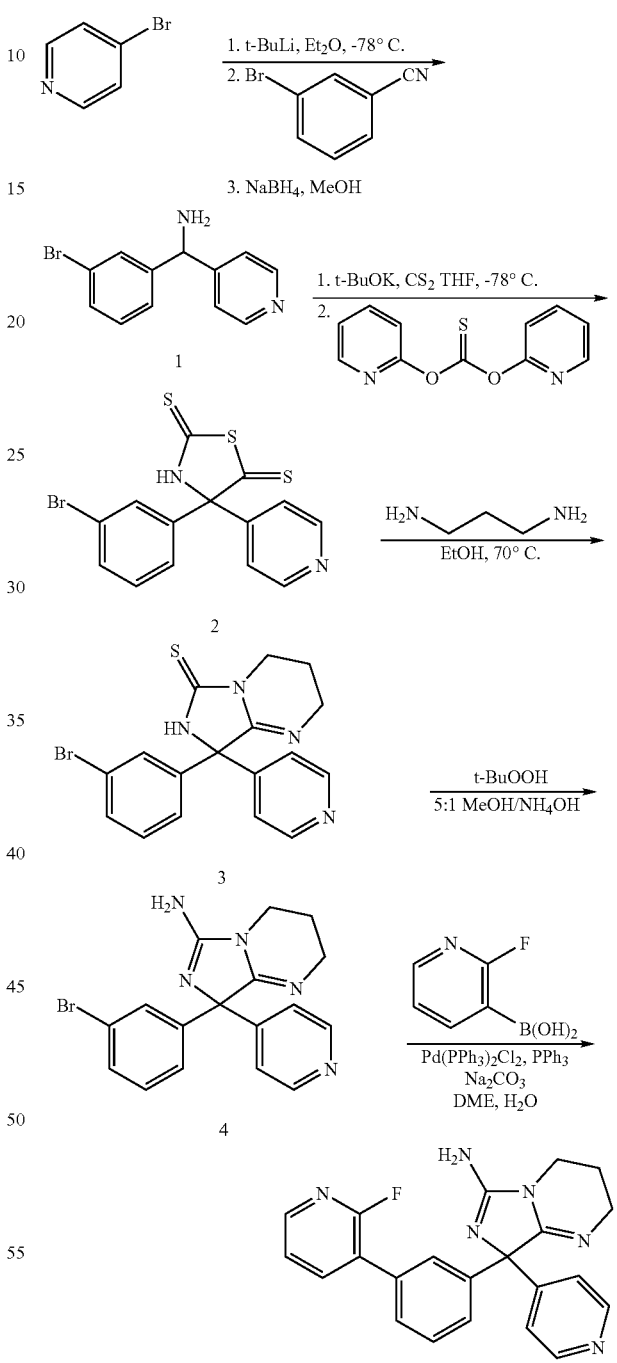

A) Preparation of Compound 1

A solution of tert-butyl lithium (30.0 mL of 1.7 M in pentane, 51.0 mmol) in diethyl ether, at −78° C., was treated dropwise with a solution of 4-bromopyridine (25.7 mmol) in diethyl ether, stirred at −78° C. for 40 min, allowed to warm to 0° C., treated sequentially with methanol and sodium borohydride (1.94 g, 51.0 mmol), stirred overnight at room temperature, diluted with saturated aqueous ammonium chloride and concentrated under reduced pressure to remove most of the methanol and diethyl ether. The resultant aqueous residue was extracted with methylene chloride. The extracts were combined, washed with brine, dried over sodium sulfate and concentrated in vacuo. Purification of this residue by flash chromatography (silica, methylene chloride to 95:5:0.25 methylene chloride/methanol/concentrated ammonium hydroxide) afforded compound 1 as a yellow syrup, 4.21 g (69% yield), $^1$H NMR (300 MHz, CDCl$_3$) δ 8.54 (dd, J=4.5, 1.5 Hz, 2H), 7.36-7.28 (m, 6H), 5.14 (s, 1H), 1.25 (s, 2H, br); ESI MS m/z 264 $[C_{12}H_{11}BrN_2+H]^+$.

B) Preparation of Compound 2

A mixture of potassium tert-butoxide (0.355 g, 3.16 mmol) in tetrahydrofuran at −78° C. was treated dropwise with a solution of 1 (0.665 g, 2.53 mmol) in tetrahydrofuran, stirred for 10 min, treated with carbon disulfide (0.635 g, 8.34 mmol), allowed to warm to room temperature slowly and stirred for 1 h at room temperature. The reaction mixture was cooled to −78° C., treated with di-2-pyridyl-thiocarbonate (0.880 g, 3.79 mmol), allowed to warm to room temperature, stirred overnight at room temperature and concentrated in vacuo. The resultant residue was purified by flash chromatography (silica, 97.5:2.5 methylene chloride/methanol) to give compound 2 as a pink oil, 0.310 g (32% yield), $^1$H NMR (300 MHz, CDCl$_3$) δ 8.66 (dd, J=4.5, 1.5 Hz, 2H), 7.57 (dt, J=6.5, 2.0 Hz, 1H), 7.47 (d, J=2.0 Hz, 1H), 7.34 (dd, J=4.5, 1.5 Hz, 2H), 7.32-7.26 (m, 2H); ESI MS m/z 381 $[C_{14}H_9BrN_2S_3+H]^+$.

C) Preparation of Compound 3

A mixture of 2 (0.310 g, 0.810 mmol) and 1,3-diaminopropane (0.181 g, 2.44 mmol) in ethanol was heated at 70° C. for 1 h, cooled to room temperature and concentrated to dryness. Purification of the resultant residue by flash chromatography (silica, 97.5:2.5:0.25 methylene chloride/methanol/concentrated ammonium hydroxide) afforded compound 3 as a white solid, 0.260 g (83% yield), $^1$H NMR (500 MHz, CD$_3$OD) δ 8.57 (dd, J=4.5, 1.5 Hz, 2H), 7.56-7.52 (m, 2H), 7.41 (dd, J=4.5, 1.5 Hz, 2H), 7.36-7.33 (m, 2H), 3.86 (t, J=6.0 Hz, 2H), 3.56 (t, J=5.5 Hz, 2H), 1.88 (tt, J=6.0, 5.5 Hz, 2H); ESI MS m/z 387 $[C_{17}H_{15}BrN_4S+H]^+$.

D) Preparation of Compound 4

A mixture of 3 (0.260 g, 0.670 mmol) and t-butyl hydroperoxide (1.73 g of a 70% solution in water, 13.4 mmol) in methanol and concentrated aqueous ammonium hydroxide was stirred overnight at room temperature and concentrated in vacuo. Purification of the resultant residue by flash chromatography (silica, 95:5:0.25 methylene chloride/methanol/concentrated ammonium hydroxide) afforded compound 4 as a white solid, 0.210 g (84% yield), $^1$H NMR (300 MHz, CDCl$_3$) δ 8.48 (dd, J=4.5, 1.5 Hz, 2H), 7.52 (t, J=1.5 Hz, 1H), 7.46 (dt, J=7.5, 1.5 Hz, 1H), 7.40 (dd, J=4.5, 1.5 Hz, 2H), 7.32 (dt, J=7.5, 1.5 Hz, 1H), 7.25 (t, J=7.5 Hz, 1H), 3.69 (t, J=6.0 Hz, 2H), 3.50 (t, J=5.1 Hz, 2H), 1.86 (tt, J=6.0, 5.1 Hz, 2H); ESI MS m/z 370 $[C_{17}H_{16}BrN_5+H]^+$.

D) Preparation of 8-[3-(2-Fluoropyridin-3-yl)phenyl]-8-pyridin-4-yl-2,3,4,8-tetrahydroimidazo[1,5-a]pyrimidin-6-amine A mixture of 4 (0.100 g, 0.27 mmol), 2-fluoropyridine-3-boronic acid (0.076 g, 0.540 mmol), bis(triphenylphosphino)palladium(II) chloride (0.010 g, 0.014 mmol), triphenylphosphine (0.0071 g, 0.027 mmol) and sodium carbonate (0.086 g, 0.810 mmol) in 3:1 DME/water was heated at reflux temperature for 2 h, cooled to room temperature and diluted with ethyl acetate and water. The phases were separated. The organic phase was washed with brine, dried over magnesium sulfate and concentrated in vacuo. Purification of the resultant residue by flash chromatography (silica, 95:5:0.25 methylene chloride/methanol/concentrated ammonium hydroxide) afforded a white solid. This material was freeze dried from 2:1 acetonitrile/water to afford the title product as a white solid, 0.082 g (79% yield), mp 125-131° C.; $^1$H NMR (500 MHz, CDCl$_3$) δ 8.16 (dd, J=4.5, 1.5 Hz, 2H), 8.16 (dt, J=5.0, 1.5 Hz, 1H), 7.83 (ddd, J=9.5, 7.5, 2.0 Hz, 1H), 7.70 (d, J=1.5 Hz, 1H), 7.52 (dt, J=8.0, 1.5 Hz, 1H), 7.47 (dd, J=4.5, 1.5 Hz, 2H), 7.47-7.46 (m, 1H), 7.41 (t, J=7.5 Hz, 1H), 7.24 (ddd, J=7.5, 5.0, 2.0 Hz, 1H), 3.62-3.57 (m, 4H), 1.88 (m, 2H); ESI MS m/z 387 $[C_{22}H_{19}FN_6+H]^+$.

EXAMPLE 2

Preparation of 8-(2,6-Diethylpyridin-4-yl)-8-[3-(2-fluoropyridin-3-yl)phenyl]-2,3,4,8-tetrahydroimidazo[1,5-a]pyrimidin-6-amine

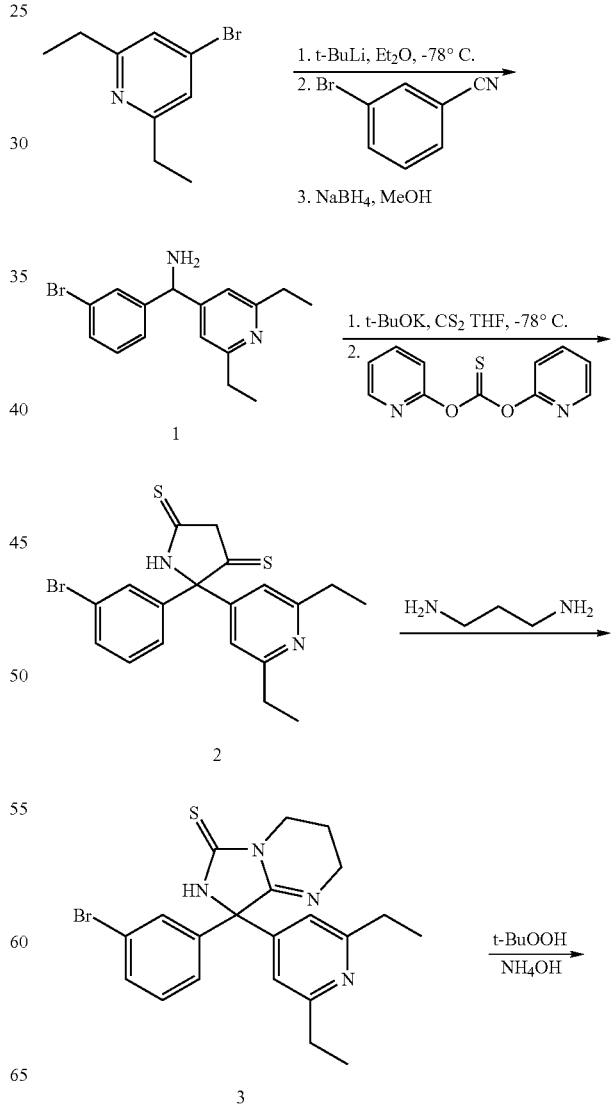

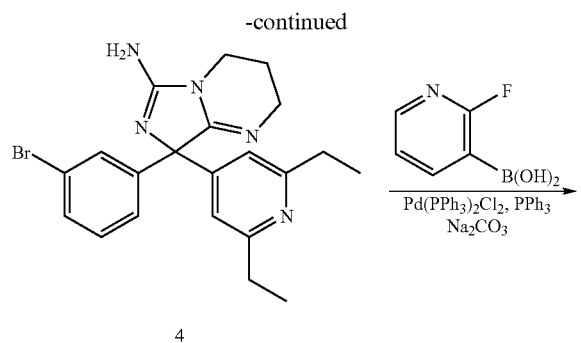

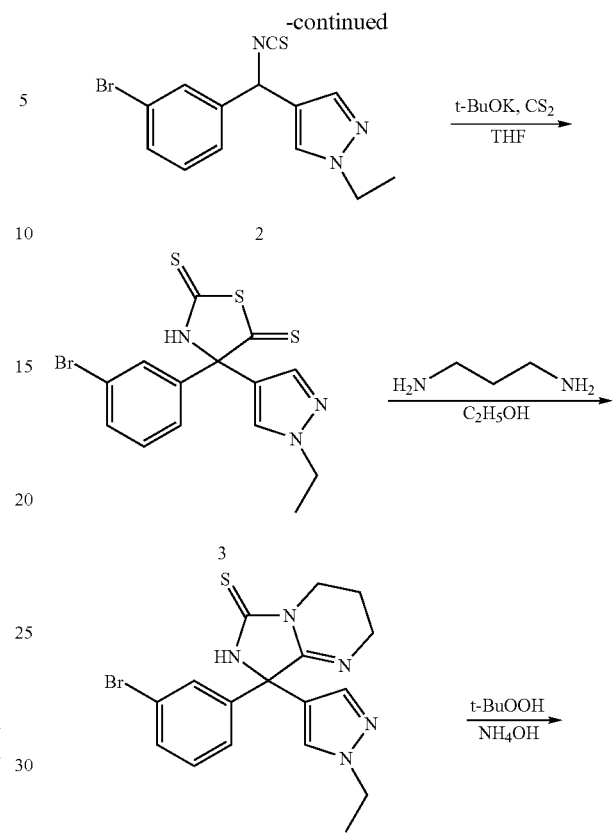

Using essentially the same procedure described in Example 1 and employing 4-Bromo-2,6-diethylpyridine in Step A, the title product is obtained as a white solid, 0.095 g, mp 174-176° C.; $^1$H NMR (500 MHz, CDCl$_3$) δ 8.16 (d, J=4.2 Hz, 1H), 8.04-7.98 (m, 1H), 7.54-7.37 (m, 5H), 7.13 (s, 2H), 3.70 (t, J=6.0 Hz, 2H), 3.50 (t, J=6.0 Hz, 2H), 2.75 (q, J=7.8 Hz, 4H), 1.87 (t, J=5.7 Hz, 2H), 1.23 (t, J=7.8 Hz, 6H); ESI MS m/z 443 [C$_{26}$H$_{27}$FN$_6$+H]$^+$

EXAMPLE 3

Preparation of 8-(1-Ethyl-1H-pyrazol-4-yl)-8-[3-(2-fluoropyridin-3-yl)phenyl]-2,3,4,8-tetrahydroimidazo[1,5-a]pyrimidin-6-amine

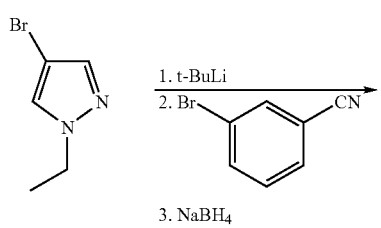

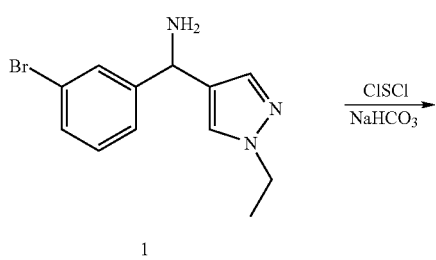

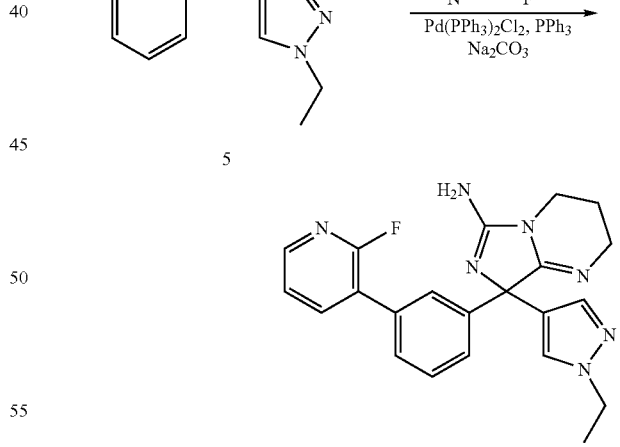

A) Preparation of Compound 1

A mixture of t-butyl lithium (16.2 mL of a 1.7 M solution in pentane, 27.5 mmol) and diethyl ether was cooled to −78° C., treated dropwise over a 15 min. period with a solution of 4-bromo-1-ethylpyrazole (2.3 g, 13.1 mmol) in diethyl ether, stirred at −78° C. for 10 min, treated dropwise with a solution of 3-bromobenzonitrile (2.58 g, 14.1 mmol) in ether, stirred at −78° C. for 45 min and allowed to warm to room temperature for1 h. The reaction mixture was treated with anhydrous methanol, cooled to 0° C., treated with sodium borohydride (0.991 g, 26.2 mmol), warmed to room temperature, stirred for 1 h at to room temperature, cooled to 0° C. and quenched by the careful addition of saturated ammonium chloride until gas evolution had ceased and all precipitates had dissolved. The reaction mixture was diluted with methylene chloride and water. The phases were separated. The organic phase was washed with brine, dried over sodium sulfate and concentrated in vacuo. Purification of the resultant residue by flash chromatography (silica, methylene chloride/methanol 95:5) afforded compound 1 as a colorless oil, 1.91 g (52% yield), $^1$H NMR (300 MHz, CDCl$_3$) δ 7.54 (br s, 1H), 7.41-7.35 (m, 2H), 7.32-7.27 (m, 1H), 7.24-7.16 (m, 2H), 5.11 (s, 1H), 4.10 (q, J=7.3 Hz, 2H), 1.89 (br s, 2H), 1.44 (t, J=7.3 Hz, 3H); ESI MS m/z 263 [(C$_{12}$H$_{14}$BrN$_3$—NH$_2$)+H]$^+$.

B) Preparation of Compound 2

A mixture of 1 (0.112 g, 0.40 mmol) in methylene chloride and saturated aqueous sodium bicarbonate was cooled with an ice bath, treated with thiophosgene (0.05 g, 0.44 mmol), stirred vigorously for 30 min and diluted with methylene chloride. The phases were separated. The organic phase was washed with brine, dried over sodium sulfate and concentrated to afford compound 2 as a yellow syrup, 0.11 g (84% yield), $^1$H NMR (300 MHz, CDCl$_3$) δ 7.51-7.45 (m, 2H), 7.37 (s, 1H), 7.31-7.24 (m, 3H), 5.93 (s, 1H), 4.14 (q, J=7.3 Hz, 2H), 1.47 (t, J=7.3 Hz, 3H).

C) Preparation of Compound 3

A mixture of potassium t-butoxide (0.04 g, 0.37 mmol) in tetrahydrofuran at −78° C. was treated dropwise over a period of 2 min. with a solution of 2 (0.11 g, 0.34 mmol) and carbon disulfide (0.04 g, 0.51 mmol) in tetrahydrofuran, stirred at −78° C. for 0.5 h, slowly warmed to room temperature, stirred at room temperature for 1 h and diluted with methylene chloride and water. The phases were separated. The organic phase was washed with brine, dried over sodium sulfate and concentrated to afford compound 3 as a yellow solid, 0.089 g (66% yield), $^1$H NMR (300 MHz, DMSO-d$_6$) δ 7.88-7.26 (m, 6H), 4.15, 4.06 (2q, J=7.3 Hz, 2H), 1.41-1.39 (m, 3H); ESI MS m/z 398 [C$_{14}$H$_{12}$BrN$_3$S$_3$+H]$^+$.

D) Preparation of Compound 4

A mixture of 3 (0.50 g, 1.25 mmol) and 1,3-diaminopropane (0.28 g, 3.75 mmol) in ethanol was heated at 70° C. for 1 h, cooled to room temperature and evaporated under reduced pressure. The resultant residue was partitioned between ethyl acetate and water. The organic phase was separated, washed with brine, dried over sodium sulfate and concentrated in vacuo to afford compound 4 as a pale yellow oil, 0.38 g (75% yield), $^1$H NMR (300 MHz, CDCl$_3$) δ 7.63 (s, 1H), 7.53-7.47 (m, 2H), 7.43-7.23 (m, 3H), 4.15 (q, J=7.3 Hz, 2H), 3.83 (t, J=6.0 Hz, 2H), 3.53-3.45 (m, 2H), 1.90-1.83 (m, 2H), 1.43 (t, J=7.3 Hz, 3H); ESI MS m/z 404 [C$_{17}$H$_{18}$BrN$_5$S+H]$^+$.

E) Preparation of Compound 5

A mixture of compound 4 (0.38 g, 0.94 mmol) and t-butyl hydroperoxide (3.6 g of a 70% solution in water, 28.2 mmol) in methanol and concentrated aqueous ammonium hydroxide was stirred overnight at room temperature, treated with 10% aqueous sodium thiosulfate (30 mL) and concentrated under reduced pressure to remove most of the methanol. The resultant aqueous mixture was extracted with methylene chloride. The extracts were combined, washed sequentially with water and brine, dried over sodium sulfate and concentrated in vacuo. Purification of this residue by flash chromatography (silica, 95:5:0.25 methylene chloride/methanol/concentrated ammonium hydroxide) afforded compound 5 as a colorless syrup, 0.09 g (25% yield), $^1$H NMR (300 MHz, CDCl$_3$) δ 7.66 (s, 1H), 7.48-7.34 (m, 4H), 7.17 (t, J=7.8 Hz, 1H), 4.11 (q, J=7.3 Hz, 2H), 3.59 (t, J=5.8 Hz, 2H), 3.58-3.52 (m, 2H), 1.91-1.80 (m, 2H), 1.46 (t, J=7.3 Hz, 3H); ESI MS m/z 387 [C$_{17}$H$_{19}$BrN$_6$+H]$^+$.

Preparation of 8-(1-Ethyl-1H-pyrazol-4-yl)-8-[3-(2-fluoropyridin-3-yl)phenyl]-2,3,4,8-tetrahydroimidazo[1,5-a]pyrimidin-6-amine A mixture of 5 (0.090 g, 0.230 mmol), 2-fluoropyridine-3-boronic acid (0.065 g, 0.460 mmol), bis(triphenylphosphino)palladium(II) chloride (0.008 g, 0.011 mmol), triphenylphosphine (0.006 g, 0.022 mmol) and sodium carbonate (0.073 g, 0.690 mmol) in 3:1 DME/water was heated at reflux temperature for 1.5 h, cooled to room temperature and diluted with ethyl acetate and water. The phases were separated. The organic phase was washed with brine, dried over magnesium sulfate and concentrated in vacuo. Purification of the resultant residue by flash chromatography (silica, 95:5:0.25 methylene chloride/methanol/concentrated ammonium hydroxide) afforded 0.035 g of an off-white solid. This material was freeze dried from 2:1 acetonitrile/water to afford a white solid, which was contaminated with dimethylformamide. Purification of this solid by flash chromatography (silica, 95:5:0.25 methylene chloride/methanol/concentrated ammonium hydroxide) to afford a white solid, which was freeze dried from 2:1 acetonitrile/water to afford the title product as a white solid, 0.034 g (35% yield), mp 91-115° C.; $^1$H NMR (300 MHz, CDCl$_3$) δ 8.20-8.12 (m, 1H), 7.90-7.81 (m, 1H), 7.71 (br s, 1H), 7.59-7.40 (m, 6H), 4.12 (q, J=7.3 Hz, 2H), 3.70 (t, J=6.0 Hz, 2H), 3.57 (t, J=4.9 Hz, 2H), 1.95-1.82 (m, 2H), 1.46 (t, J=7.3 Hz, 3H); ESI MS m/z 404 [C$_{22}$H$_{22}$FN$_7$+H]$^+$.

EXAMPLE 4

Preparation of 8-[3-(2-Fluoropyridin-3-yl)phenyl]-8-[1-(2,2,2-trifluoroethyl)-1H-pyrazol-4-yl]-2,3,4,8-tetrahydroimidazo[1,5-a]pyrimidin-6-amine

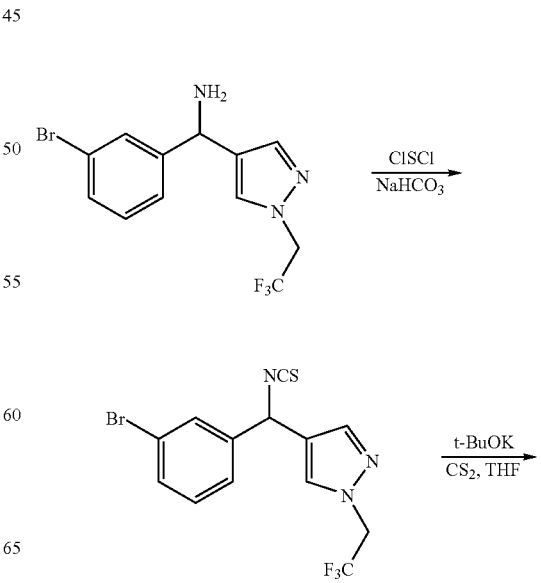

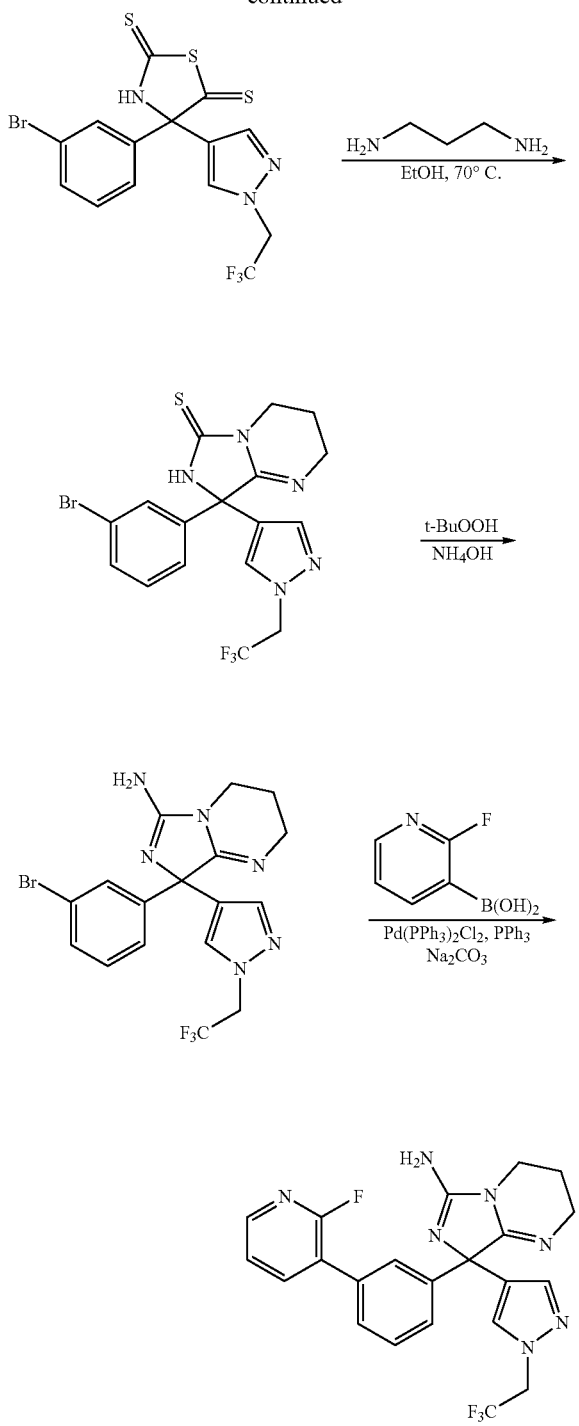
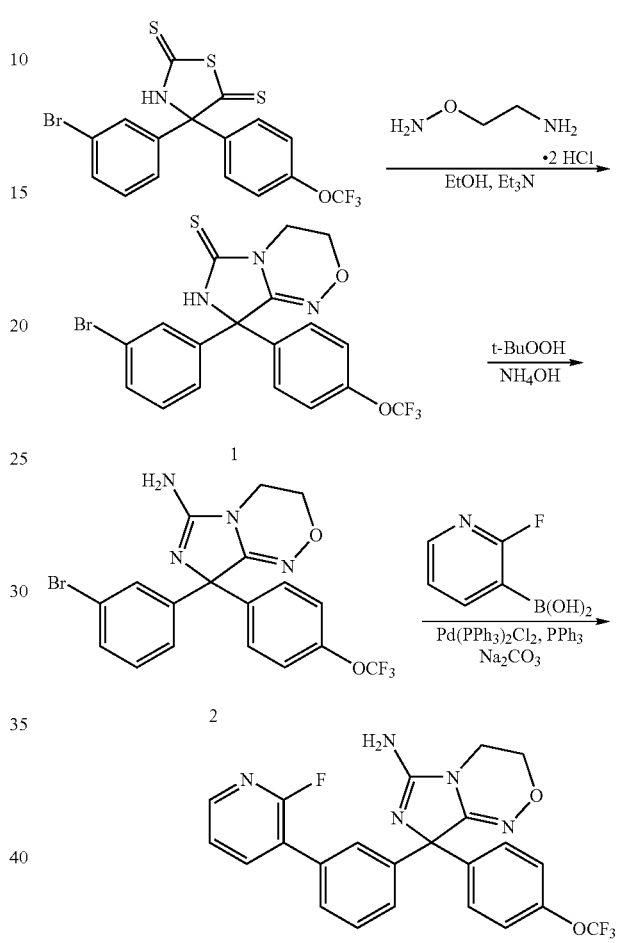

Using essentially the same procedure described in Example 3 and employing 1(4-bromophenyl)-1-[(2,2,2-trifluoroethyl)pyrazol-4-yl]methylamine in Step B, the title product was obtained as a white solid, mp 106-116° C., $^1$H NMR (300 MHz, CDCl$_3$) δ 8.17 (dd, J=1.7, 1.6 Hz, 1H), 7.82 (m, 1H), 7.68 (d, J=1.4 Hz, 1H), 7.63 (s, 1H), 7.59 (s, 1H), 7.57-7.41 (m, 3H), 7.23 (m, 1H), 4.68 (q, J=8.4 Hz, 2H), 3.60 (t, J=5.9 Hz, 2H), 3.54 (m, 2H), 1.85 (m, 2H); ESI MS m/z 458 [C$_{22}$H$_{19}$F$_4$N$_7$+H]$^+$.

EXAMPLE 5

Preparation of 8-[3-(2-Fluoropyridin-3-yl)phenyl]-8-[4-(trifluoromethoxy)-phenyl]-3,4-dihydro-8H-imidazo[5,1-c][1,2,4]oxadiazin-6-amine A) Preparation of Compound 1

A mixture of 4-(3-bromophenyl)-4-[4-(trifluoromethoxy)phenyl]-1,3-thiazolidine-2,5-dithione (0.50 g, 1.08 mmol), 2-(aminooxy)ethanamine (0.48 g, 3.23 mmol, prepared as described in *J. Med. Chem.* 2000, 43(12), 2347) and triethylamine (0.71 g, 7.00 mmol) in ethanol was stirred at ice bath temperatures for 2 h, warmed to room temperature, stirred at room temperature for 24 h, heated to 70° C., stirred at 70° C. for 2 h, cooled to room temperature and concentrated under reduced pressure. The resultant residue was partitioned between ethyl acetate and water. The organic phase was washed sequentially with 1 N HCl and brine, dried over magnesium sulfate and concentrated in vacuo. Purification of this residue by flash chromatography (silica, 1:5 ethyl acetate/hexanes) afforded compound 1 as a white solid, 0.277 g (54% yield), $^1$H NMR (300 MHz, CDCl$_3$) δ 7.53 (m, 2H), 7.39 (d, J=8.9 Hz, 2H), 7.38-7.22 (m, 4H), 4.11 (m, 2H), 4.03 (m, 2H); ESI MS m/z 472 [C$_{18}$H$_{13}$BrF$_3$N$_3$O$_2$S+H]$^+$.

B) Preparation of Compound 2

A mixture of compound 1 (0.27 g, 0.571 mmol) and t-butyl hydroperoxide (1.47 g of a 70% solution in water, 11.4 mmol)

in methanol and concentrated aqueous ammonium hydroxide was stirred overnight at room temperature, treated with 10% aqueous sodium thiosulfate and concentrated to remove most of the methanol. The resultant aqueous mixture was extracted with methylene chloride. The extracts were combined, washed with brine, dried over magnesium sulfate and concentrated in vacuo. Purification of this concentrate by flash chromatography (silica, 95:5:0.25 methylene chloride/methanol/concentrated ammonium hydroxide) afforded compound 2 as a white solid, 0.166 g (64% yield), $^1$H NMR (300 MHz, CDCl$_3$) δ 7.70 (t, J=1.8 Hz, 1H), 7.56 (m, 1H). 7.45-7.37 (m, 3H), 7.20-7.13 (m, 3H), 3.99 (m, 2H), 3.77 (m, 2H); ESI MS m/z 456 $[C_{18}H_{14}BrF_3N_4O_2+H]^+$.

C) Preparation of 8-[3-(2-Fluoropyridin-3-yl)phenyl]-8-[4(trifluoromethoxy)-phenyl]-3,4dihydro-8H-imidazo[5,1-c][1,2,4]oxadiazin-6-amine A mixture of 2 (0.16 g, 0.351 mmol), 2-fluoropyridine-3-boronic acid (0.089 g, 0.633 mmol), bis(triphenylphosphino)palladium(II) chloride (0.012 g, 0.018 mmol), triphenylphosphine (0.0092 g, 0.035 mmol) and sodium carbonate (0.112 g, 1.05 mmol) in 3:1 DME/water was heated at reflux for 3 h, cooled to room temperature and diluted with ethyl acetate and water. The organic phase was separated, washed with brine, dried over magnesium sulfate and concentrated. Purification of the resuntant concentrate by flash chromatography (silica, 95:5:0.25 methylene chloride/methanol/concentrated ammonium hydroxide) afforded 0.12 g of a white solid. This material was freeze dried from 2:1 acetonitrile/water (6 mL) to afford the title product as a white solid, 0.109 g (66% yield), mp 102-117° C.; $^1$H NMR (300 MHz, CDCl$_3$) δ 8.16 (m, 1H), 7.83 (m, 1H), 7.71 (m, 1H), 7.61-7.56 (m, 3H), 7.46-7.41 (m, 2H), 7.25 (m, 1H), 7.15 (m, 2H), 4.00 (m, 2H), 3.78 (m, 2H); ESI MS m/z 472 $[C_{23}H_{17}F_4N_5O_2+H]^+$.

EXAMPLE 6

Preparation of 8-[3-(5-Fluoropyridin-3-yl)phenyl]-8-[4-(trifluoromethoxy)phenyl]-2,8-dihydro-3H-imidazo[1,5-b][1,2,4]oxadiazin-6-amine

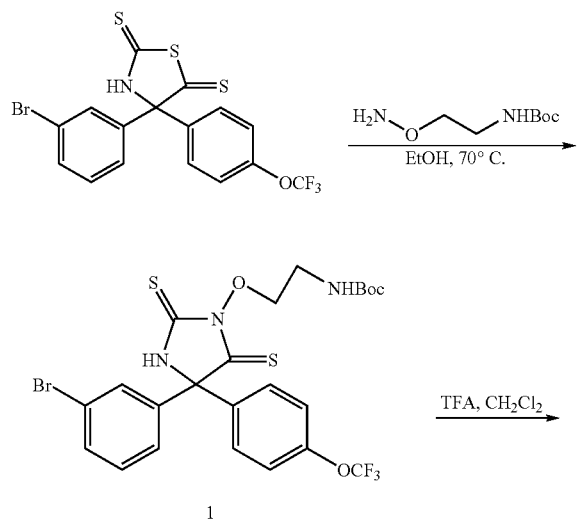

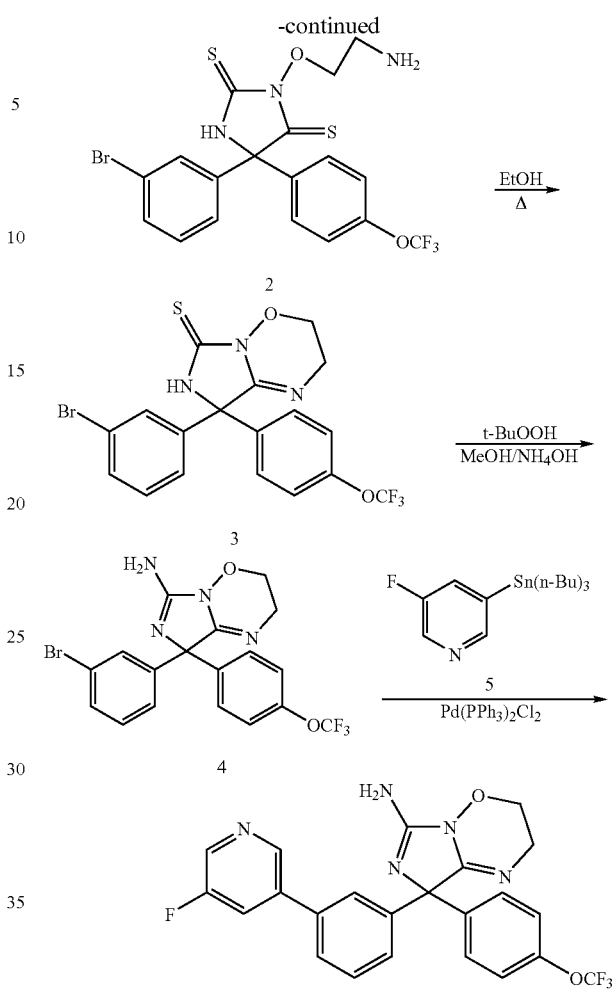

A) Preparation of Compound 1

A mixture of 4-(3-bromophenyl)-4-[4-(trifluoromethoxy)phenyl]-1,3-thiazolidine-2,5-dithione (1.32 g, 2.84 mmol) and Boc-protected 2-(aminooxy)ethanamine (1.49 g, 8.53 mmol) in ethanol was stirred at 70° C. for 1.5 h, cooled to room temperature and concentrated under reduced pressure. The resultant residue was partitioned between ethyl acetate and water. The organic phase was separated, washed with brine, dried over sodium sulfate and concentrated in vacuo. Purification of this residue by flash chromatography ( silica, 1:4 ethyl acetate/hexanes) afforded compound 1 as a white solid, 1.12 g (65% yield), $^1$H NMR (500 MHz, CDCl$_3$) δ 7.72 (bs, 1H), 7.56 (dt, J=4.1, 1.6 Hz, 1H), 7.49 (d, J=1.8 Hz, 1H), 7.38 (d, J=8.7 Hz, 2H), 7.30 (m, 3H), 4.68 (bs, 1H), 4.21 (t, J=5.1 Hz, 2H), 3.37 (bs, 2H), 1.43 (s, 9H); ESI MS m/z 607 $[C_{23}H_{23}BrF_3N_3O_4S_2+H]^+$.

B) Preparation of Compound 2

A mixture of compound 1 (1.12 g, 1.85 mmol), trifluoroacetic acid (6.0 mL) and methylene chloride was stirred at ambient temperatures for 1 h and concentrated under reduced pressure. The concentrate was basified with 10% aqueous potassium carbonate to pH 9 and extracted with methylene chloride. The extracts were combined, dried over sodium sulfate and concentrated to afford compound 2 as an off-white solid, 0.842 g (90% yield), $^1$H NMR (500 MHz, CDCl$_3$) δ

7.21-7.60 (m, 6H), 7.11-7.25 (m, 2H), 4.22 (t, J=5.3 Hz, 2H), 2.94 (t, J=5.2 Hz, 2H), 1.62 (s, 2H); ESI MS m/z 507 $[C_{18}H_{15}BrF_3N_3O_2S_2+H]^+$.

C) Preparation of Compound 3

A solution of compound 2 (0.842 g, 1.66 mmol) in ethanol was heated at reflux temperature for 1 h, cooled to room temperature and concentrated in vacuo. The resultant residue was purified by flash chromatography (silica, 3:1 hexanes/ethyl acetate) to afford compound 3 as an off-white solid, 0.437 g (56% yield), $^1$H NMR (500 MHz, CDCl$_3$) δ 7.63 (m, 2H), 7.39 (dd, J=4.6, 2.1 Hz, 2H), 7.28 (m, 2H), 7.23 (d, J=8.0 Hz, 2H), 4.11 (t, J=2.9 Hz, 2H), 4.02 (t, J=3.2 Hz, 2H); ESI MS m/z 473 $[C_{18}H_{13}BrF_3N_3O_2S+H]^+$;

D) Preparation of Compound 4

A mixture of compound 3 (0.434 g, 0.920 mmol) and t-butyl hydroperoxide (3.55 g of a 70% solution in water, 27.6 mmol) in methanol and concentrated aqueous ammonium hydroxide was stirred overnight at room temperature, treated with 10% aqueous sodium thiosulfate and concentrated to remove most of the methanol. The resultant aqueous mixture was extracted with methylene chloride. The extracts were combined, dried over sodium sulfate and concentrated to dryness. Purification of this residue by flash chromatography (silica, 95:5:0.25 methylene chloride/methanol/concentrated ammonium hydroxide) afforded compound 4 as an off white solid, 0.284 g (68% yield), $^1$H NMR (500 MHz, CDCl$_3$) δ 7.69 (t, J=1.8 Hz, 1H), 7.55 (dd, J=4.7, 2.1 Hz, 2H), 7.42 (dt, J=5.2, 1.0 Hz, 1H), 7.40 (dt, J=6.0, 1.0 Hz, 1H), 7.18 (m, 3H), 4.00 (t, J=4.5 Hz, 2H), 3.79 (t, J=6.1 Hz, 2H); ESI MS m/z 456 $[C_{18}H_{14}BrF_3N_4O_2+H]^+$.

E) Preparation of 8-[3-(5-Fluoropyridin-3-yl)phenyl]-8-[4-(trifluoromethoxy)-phenyl]-2,8-dihydro-3H-imidazo[1,5-b][1,2,4]oxadiazin-6-amine A mixture of compound 4 (0.095 g, 0.209 mmol), compound 5 (0.122 g, 0.313 mmol), and dichlorobis(triphenylphosphine)palladium(II) (0.007 g, 0.011 mmol) in DMF was degassed then heated at 150° C. in a sealed tube for 1.5 h. The mixture was cooled to room temperature and diluted with ethyl acetate and 5% aqueous LiCl. The organic phase was separated, washed with 5% aqueous LiCl, dried over sodium sulfate and concentrated in vacuo. Purification of the resultant residue by flash chromatography (silica, 95:5:0.25 methylene chloride/methanol/concentrated ammonium hydroxide) afforded the title product as a white solid, 0.050 g (38% yield), mp 120-135° C., $^1$H NMR (500 MHz, CDCl$_3$) δ 8.67 (bs, 1H), 8.38 (d, J=2.3 Hz, 1H), 7.78 (bs, 1H), 7.45-7.62 (m, 6H), 7.18 (d, J=8.3 Hz, 2H), 4.05 (bs, 2H), 3.99 (bs, 2H); ESI MS m/z 472 $[C_{23}H_{17}F_4N_5O_2+H]^+$.

EXAMPLE 7

Evaluation of the Enzyme Activity of Test Compounds and the Inhibition of hBACE1, MuBACE1 and hBACE2 by Test Compounds Assay Conditions: 10 nM human BACE1 (or 10 nM Murine BACE1, 1.5 nM human BACE2) 25 μM substrate (WABC-6, MW 1549.6, from AnaSpec); final buffer conditions: 50 mM Na-Acetate, pH 4.5, 0.05% CHAPS, 25% PBS; temperature: room temperature; reagent information: Na-Acetate: Aldrich, Cat.#24,124-5 CHAPS: Research Organics, Cat. #1304C 1× PBS: Mediatech (Cellgro), Cat#21-031-CV; peptide substrate AbzSEVNLDAEFRDpa: AnaSpec, Peptide Name: WABC-6; determination of stock substrate (AbzSEVNLDAEFRDpa) concentration: a 25 mM stock solution in dimethyl sulfoxide (DMSO) is prepared using the peptide weight and MW and diluted to 25 μM. The concentration is determined by absorbance at 354 nm using an extinction coefficient ε of 18172 M$^{-1}$ cm$^{-1}$, The substrate stock is stored in small aliquots at −80° C. [Substrate Stock]= $ABS^{354\ nm}*10^6/18172$ (in mM)

Determination of Stock Enzyme Concentration: The stock concentration of each enzyme by ABS at 280 nm using □ of 64150 M$^{-1}$ cm$^{-1}$ for hBACE1 and MuBACE1, 62870 M$^{-1}$ cm$^{-1}$ for hBACE2 in 6 M Guanidinium Hydrochloride (from Research Organics, Cat. #5134G-2), pH 6.

(The extinction coefficient $\epsilon^{280\ nm}$ for each enzyme was calculated based on known amino acid composition and published extinction coefficients for Trp (5.69 M$^{-1}$ cm$^{-1}$) and Tyr (1.28 M$^{-1}$ cm$^{-1}$) residues (*Anal. Biochem.* 182, 319-326).

Dilution and mixing steps: total reaction volume: 100 μL
1. 2× inhibitor dilutions in buffer A (66.7 mM Na-Acetate, pH 4.5, 0.0667% CHAPS) are prepared,
2. 4× enzyme dilution in buffer A (66.7 mM Na-Acetate, pH 4.5, 0.0667% CHAPS) are prepared,
3. 100 μM substrate dilution in 1× PBS is prepared,
4. 50 μL 2× Inhibitor and 25 μL 100 μM substrate are added to each well of 96-well plate (from DYNEX Technologies, VWR #: 11311-046), the immediately 25 μL 4× enzyme are added to the inhibitor and substrate mixer, the fluorescence readings are initiated.

Fluorescence Readings: Readings at $\lambda_{ex}$ 320 nm and $\lambda_{em}$ 420 nm are taken every 40-sec for 30 min at room temperature to determine the linear slope for substrate cleavage rate ($v_i$).

Calculation of % Inhibition: % Inhibition=100*(1−$v_i$/$v_0$) ($v_i$=substrate cleavage rate in the presence of inhibitor, $v_0$=substrate cleavage rate in the absence of inhibitor)

$$IC_{50}\ \text{Determination: \% Inhibition}=[(B*IC_{50}^n)+(100*I_0^n)]/(IC_{50}^n+I_0^n),$$

Fluorescent Kinetic Assay for Human Recombinant BACE 2

This assay is used to provide kinetic and selectivity parameters for the analyses of the tested compounds.

Materials and methods: final assay conditions: 10 nM human BACE1 (or 10 nM Murine BACE1, 1.5 nM human BACE2) 25 μM Substrate (WABC-6, MW 1549.6, from AnaSpec). Final buffer conditions: 50 mM Na-Acetate, pH 4.5, 0.05% CHAPS, 25% PBS. Temperature: room temperature. Reagent Information: Na-Acetate: Aldrich, Cat.#24, 124-5 CHAPS: Research Organics, Cat. #1304C 1× PBS: Mediatech (Cellgro), Cat#21-031-CV Peptide Substrate AbzSEVNLDAEFRDpa: AnaSpec, Peptide Name: WABC-6

Determination of stock substrate (AbzSEVNLDAEFRDpa) concentration: A 25 mM stock solution in DMSO is prepared using the peptide weight and MW, and diluted to 25 μM. The concentration is determined by absorbance at 354 nm using an extinction coefficient ε of 18172 M$^{-1}$cm$^{-1}$. The substrate stock is stored in small aliquots at −80° C. [Substrate Stock]=$ABS^{354\ nm}*10^6/18172$ (in mM)

Determination of stock enzyme concentration: The stock concentration of each enzyme is determined by ABS at 280 nm using ε of 64150 M$^{-1}$cm$^{-1}$ for hBACE1 and MuBACE1, 62870 M$^{-1}$cm$^{-1}$ for hBACE2 in 6 M guanidinium hydrochloride (from Research Organics, Cat. #5134G-2), pH 6. (The extinction coefficient $\epsilon^{280\ nm}$ for each enzyme is calculated based on known amino acid composition and published extinction coefficients for Trp (5.69 M$^{-1}$ cm$^{-1}$) and Tyr (1.28 M$^{-1}$ cm$^{-1}$) residues (*Anal. Biochem.* 182, 319-326).)

Dilution and Mixing Steps: Total Reaction Volume: 100 μL
1. 2× inhibitor dilutions in buffer A (66.7 mM Na-Acetate, pH 4.5, 0.0667% CHAPS) are prepared, 2. 4× enzyme dilution in buffer A (66.7 mM Na-Acetate, pH 4.5, 0.0667% CHAPS) are prepared,
3. 100 μM substrate dilution in 1× PBS, 50 μL 2× Inhibitor and 25 μL 100 μM substrate are added to each well of 96-well plate (from DYNEX Technologies, VWR #: 11311-046), then immediately 25 μL 4× enzyme is added to the inhibitor and substrate mixer and the fluorescence readings are initiated.

Fluorescence Readings: Readings at $\lambda_{ex}$ 320 nm, $\lambda_{em}$ 420 nm are taken every 40-sec for 30 min at room temperature and to determine the linear slope for substrate cleavage rate ($v_i$).

Analysis of calculation of % inhibition: % Inhibition=100* $(1-v_i/v_0)$ $v_i$=substrate cleavage rate in the presence of inhibitor,
$v_0$=substrate cleavage rate in the absence of inhibitor)
$IC_{50}$ Determination:

% Inhibition=$((B*IC_{50}^n)+(100*I_0^n))/(IC_{50}^n+I_0^n)$,

The data obtained are shown in Table I below. Unless otherwise noted, the $IC_{50}$ value represents the value obtained at 100% inhibition.

TABLE I

| Example Number | BACE1 IC50 | BACE2 IC50 |
|---|---|---|
| 1 | 0.52 | 51% at 25 μM |
| 2 | 0.01 | 38% at 25 μM |
| 3 | 0.09 | 3.52 |
| 4 | 0.08 | 5.12 |
| 5 | 0.03 | 2.02 |
| 6 | 0.05 | 1.19 |

Results and Discussion:

As can be seen from the data shown on Table I hereinabove, the compounds of the invention are potent and selective inhibitors of BACE1.

What is claimed is:
1. A compound of formula I

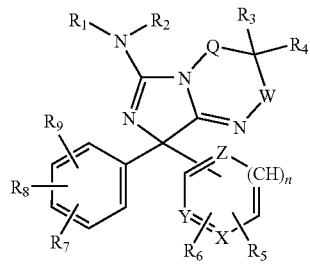

(I)

wherein
Q is $CH_2$;
W is $CH_2$;
X is N, or NO;
Y is N, NO or $CR_{10}$;
Z is N, NO or $CR_{11}$;
m is 0, 1 or 2;
n is 0 or 1;
$R_1$ and $R_2$ are each independently H or $C_1$-$C_4$ alkyl;
$R_3$ and $R_4$ are each independently H, or $C_1$-$C_4$ alkyl;
$R_5$ and $R_6$ are each independently H, halogen, $NO_2$, CN, $OR_{12}$, $CO_2R_{13}$, $COR_{14}$, $NR_{17}R_{18}$, $SO_pNR_{19}R_{20}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl;

$R_7$ and $R_8$ are each independently H, halogen, $NO_2$, CN, $OR_{15}$, $NR_{17}R_{18}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or cycloheteroalkyl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl or when attached to adjacent carbon atoms $R_7$ and $R_8$ may be taken together with the atoms to which they are attached to form an optionally substituted 5- to 7-membered ring optionally containing one or two heteroatoms selected from O, N or S;

$R_9$ is H, halogen, $NO_2$, CN, $OR_{15}$, $NR_{17}R_{18}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl;

$R_{10}$ and $R_{11}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl or aryl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl;

$R_{12}$, $R_{13}$, $R_{14}$ and $R_{15}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl;

$R_{17}$, $R_{18}$, $R_{19}$ and $R_{20}$ are each independently H, $C_1$-$C_4$alkyl, $C_3$-$C_8$cycloalkyl or $R_{17}$ and $R_{18}$ or $R_{19}$ and $R_{20}$ may be taken together with the atom to which they are attached to form a 5- to 7-membered ring optionally containing an additional heteroatom selected from O, N or S; and p is 0, 1 or 2; or a tautomer thereof, a stereoisomer thereof or a pharmaceutically acceptable salt thereof.

2. The compound according to claim 1 wherein $R_1$ and $R_2$ are H.

3. The compound according to claim 1 wherein $R_9$ is a heteroaryl group optionally substituted as in claim 1.

4. The compound according to claim 1 wherein X is N.

5. The compound according to claim 1 wherein $R_3$ and $R_4$ are H.

6. The compound according to claim 2 wherein $R_9$ is a heteroaryl group optionally substituted as in claim 1 and $R_9$ is attached to the phenyl ring in the 3-position of the phenyl ring.

7. The compound according to claim 6 wherein X is N.

8. The compound according to claim 7 wherein $R_3$ and $R_4$ are H.

9. The compound according to claim 1 selected from the group consisting essentially of:

8-[3-(2-fluoropyridin-3-yl)-phenyl]-8-pyridin-4-yl-2,3,4,8-tetrahydroimidazo[1,5-a]pyrimidin-6-amine;

8-(2,6-diethylpyridin-4-yl)-8-[3-(2-fluoropyridin-3-yl)-phenyl]-2,3,4,8-tetrahydro-imidazo[1,5-a]pyrimidin-6-amine;

8-(1-ethyl-1H-pyrazol-4-yl)-8-[3-(2-fluoropyridin-3-yl)phenyl]-2,3,4,8-tetrahydro-imidazo[1,5-a]pyrimidin-6-amine;

8-[3-(2-fluoropyridin-3-yl)phenyl]-8-[1-(2,2,2-trifluoroethyl)-1H-pyrazol-4-yl]-2,3,4,8-tetrahydroimidazo[1,5-a]pyrimidin-6-amine;

a tautomer thereof a stereoisomer thereof; and a pharmaceutically acceptable salt thereof.

10. A method for the treatment, or amelioration of a disease or disorder characterized by elevated β-amyloid deposits or β-amyloid levels in a patient which comprises providing said patient with a therapeutically effective amount of a compound of formula I

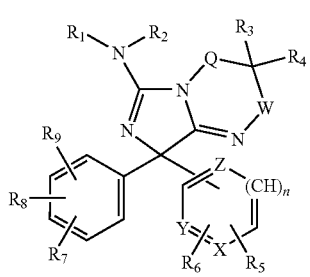

(I)

wherein

Q is $CH_2$;

W is $CH_2$;

X is N, or NO;

Y is N, NO or $CR_{10}$;

Z is N, NO or $CR_{11}$;

m is 0, 1 or 2;

n is 0 or 1;

$R_1$ and $R_2$ are each independently H or $C_1$-$C_4$ alkyl;

$R_3$ and $R_4$ are each independently H, or $C_1$-$C_4$ alkyl;

$R_5$ and $R_6$ are each independently H, halogen, $NO_2$, CN, $OR_{12}$, $CO_2R_{13}$, $COR_{14}$, $NR_{17}R_{18}$, $SO_pNR_{19}R_{20}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsuiphonyl, carbamoyl, $C_1$-$C_{12}$ alkylamido, phenyl, phenoxy, benzyl, benzyloxy, heterocyclyl or cycloalkyl;

$R_7$ and $R_8$ are each independently H, halogen, $NO_2$, CN, $OR_{15}$, $NR_{17}R_{18}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or cycloheteroalkyl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkylor when attached to adjacent carbon atoms $R_7$ and $R_8$ may be taken together with the atoms to which they are attached to form an optionally substituted 5- to 7-membered ring optionally containing one or two heteroatoms selected from O, N or S;

$R_9$ is H, halogen, $NO_2$, CN, $OR_{15}$, $NR_{17}R_{18}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsuiphonyl, carbamoyl, $C_1$-$C_{12}$ alkylamido, phenyl, phenoxy, benzyl, benzyloxy, heterocyclyl or cycloalkyl;

$R_{10}$ and $R_{11}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl or aryl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsuiphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl;

$R_{12}$, $R_{13}$, $R_{14}$ and $R_{15}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl;

$R_{17}$, $R_{18}$, $R_{19}$ and $R_{20}$ are each independently H, $C_1$-$C_4$alkyl, $C_3$-$C_8$cycloalkyl or $R_{17}$ and $R_{18}$ or $R_{19}$ and $R_{20}$ may be taken together with the atom to which they are attached to form a 5- to 7-membered ring optionally containing an additional heteroatom selected from O, N or S; and p is 0, 1 or 2; or a tautomer thereof, a stereoisomer thereof or a pharmaceutically acceptable salt thereof, wherein said disease or disorder is selected from the group consisting of: Alzheimer's disease; Down's Syndrome; Hereditary Cerebral Hemorrhage with Amyloidosis of the Dutch-type; senile dementia; and cerebral amyloid angiopathy.

11. A method for inhibiting the activity of BACE in vitro which comprises contacting a receptor thereof with an effective amount of a compound of claim 1.

12. A method for the treatment of Alzheimer's disease in a patient in need thereof which comprises providing to said patient an effective amount of a compound of claim 1.

13. A pharmaceutical composition which comprises a pharmaceutically acceptable carrier and an effective amount of a compound of formula I $$\text{(I)}$$

wherein

Q is $CH_2$;

W is $CH_2$;

X is N, or NO;

Y is N, NO or $CR_{10}$;

Z is N, NO or $CR_{11}$;

m is 0, 1 or 2;

n is 0 or 1;

$R_1$ and $R_2$ are each independently H or $C_1$-$C_4$alkyl;

$R_3$ and $R_4$ are each independently H, or $C_1$-$C_4$ alkyl;

$R_5$ and $R_6$ are each independently H, halogen, $NO_2$, CN, $OR_{12}$, $CO_2R_{13}$, $COR_{14}$, $NR_{17}R_{18}$, $SO_pNR_{19}R_{20}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl;

$R_7$ and $R_8$ are each independently H, halogen, $NO_2$, CN, $OR_{15}$, $NR_{17}R_{18}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or cycloheteroalkyl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkylor when attached to adjacent carbon atoms $R_7$ and $R_8$ may be taken together with the atoms to which they are attached to form an optionally substituted 5- to 7-membered ring optionally containing one or two heteroatoms selected from O, N or S;

$R_9$ is H, halogen, $NO_2$, CN, $OR_{15}$, $NR_{17}R_{18}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl;

$R_{10}$ and $R_{11}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl or aryl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl;

$R_{12}$, $R_{13}$, $R_{14}$ and $R_{15}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsuiphinyl, $C_1$-$C_{12}$ alkylsuiphonyl, carbamoyl, $C_1$-$C_{12}$ alkylamido, phenyl, phenoxy, benzyl, benzyloxy, heterocyclyl or cycloalkyl;

$R_{17}$, $R_{18}$, $R_{19}$ and $R_{20}$ are each independently H, $C_1$-$C_4$alkyl, $C_3$-$C_8$cycloalkyl or and $R_{18}$ or $R_{19}$ and $R_{20}$ may be taken together with the atom to which they are attached to form a 5- to 7-membered ring optionally containing an additional heteroatom selected from O, N or S; and p is 0, 1 or 2; or a tautomer thereof, a stereoisomer thereof or a pharmaceutically acceptable salt thereof.

14. The composition according to claim 13 having a formula I compound wherein $R_1$ and $R_2$ are H.

15. The composition according to claim 14 having a formula I compound wherein X is N and $R_3$ and $R_4$ are H.

16. The composition according to claim 15 having a formula I compound wherein $R_9$ is an optionally substituted heteroaryl group and is attached to the phenyl ring in the 3-position of the phenyl ring.

17. The composition according to claim 14 having a formula I compound selected from the group consisting essentially of:

8-[3-(2-fluoropyridin-3-yl)-phenyl]-8-pyridin-4-yl-2,3,4, 8-tetrahydroimidazo[1,5-a]pyrimidin-6-amine;

8-(2,6-diethylpyridin-4-yl)-8-[3-(2-fluoropyridin-3-yl)-phenyl]-2,3,4,8-tetrahydro-imidazo[1,5-a]pyrimidin-6-amine;

8-(1-ethyl-1H-pyrazol-4-yl)-8-[3-(2-fluoropyridin-3-yl)phenyl]-2,3,4,8-tetrahydro-imidazo[1,5-a]pyrimidin-6-amine;

8-[3-(2-fluoropyridin-3-yl)phenyl]-8-[1-(2,2,2-trifluoro-ethyl)-1H-pyrazol-4-yl]-2,3,4,8-tetrahydroimidazo[1,5-a]pyrimidin-6-amine;

a tautomer thereof;

a stereoisomer thereof and a pharmaceutically acceptable salt thereof.

18. A process for the preparation of a compound of formula Ia

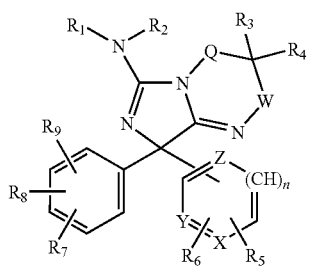

wherein

Q is $CH_2$;

W is $CH_2$;

X is N, or NO;

Y is N, NO or $CR_{10}$;

Z is N, NO or $CR_{11}$;

m is 0, 1 or 2;

n is 0 or 1;

$R_1$ and $R_2$ are each independently H or $C_1$-$C_4$alkyl;

$R_3$ and $R_4$ are each independently H, or $C_1$-$C_4$ alkyl;

$R_5$ and $R_6$ are each independently H, halogen, $NO_2$, CN, $OR_{12}$, $CO_2R_{13}$, $COR_{14}$, $NR_{17}R_{18}$, $SO_pNR_{19}R_{20}$ or a $C_1$-$C_6$alkyl, $C_1$-$C_6$haloalkyl, $C_2$-$C_6$alkenyl, $C_2$-$C_6$alkynyl or $C_3$-$C_8$cycloalkyl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl;

$R_7$ and $R_8$ are each independently H, halogen, $NO_2$, CN, $OR_{15}$, $NR_{17}R_{18}$ or a $C_1$-$C_6$alkyl, $C_1$-$C_6$haloalkyl, $C_2$-$C_6$alkenyl, $C_2$-$C_6$alkynyl, $C_3$-$C_8$cycloalkyl or cycloheteroalkyl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsuiphinyl, $C_1$-$C_{12}$ alkylsuiphonyl, carbamoyl, $C_1$-$C_{12}$ alkylamido, phenyl, phenoxy, benzyl, benzyloxy, heterocyclyl or cycloalkylor when attached to adjacent carbon atoms $R_7$ and $R_8$ may be taken together with the atoms to which they are attached to form an optionally substituted 5- to 7-membered ring optionally containing one or two heteroatoms selected from O, N or S;

$R_9$ is aryl or heteroaryl group optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alky)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsuiphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl;

$R_{10}$ and $R_{11}$ are each independently H or a $C_1$-$C_6$alkyl, $C_1$-$C_6$haloalkyl, $C_2$-$C_6$alkenyl, $C_2$-$C_6$alkynyl, $C_3$-Cscycloalkyl, cycloheteroalkyl or aryl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl) amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsuiphinyl, $C_1$-$C_{12}$ alkylsuiphonyl, carbamoyl, $C_1$-$C_{12}$ alkylamido, phenyl, phenoxy, benzyl, benzyloxy, heterocyclyl or cycloalkyl;

$R_{12}$, $R_{13}$, $R_{14}$ and $R_{15}$ are each independently H or a $C_1$-$C_6$alkyl, $C_1$-$C_6$haloalkyl, $C_2$-$C_6$alkenyl, $C_2$-$C_6$alkynyl, $C_3$-$C_8$cycloalkyl, cycloheteroalkyl, aryl or heteroaryl group each optionally substituted with 1-3 substituents selected from halogen, nitro, cyano, thiocyanato, cyanato, hydroxyl, $C_1$-$C_{12}$ alkyl, $C_1$-$C_{12}$ haloalkyl, $C_1$-$C_{12}$ alkoxy, $C_1$-$C_{12}$ haloalkoxy, amino, $C_1$-$C_{12}$ alkylamino, di($C_1$-$C_{12}$ alkyl)amino, formyl, $C_1$-$C_{12}$ alkoxycarbonyl, carboxyl, $C_1$-$C_{12}$ alkanoyl, $C_1$-$C_{12}$ alkylthio, $C_1$-$C_{12}$ alkylsulphinyl, $C_1$-$C_{12}$ alkylsulphonyl, carbamoyl, $C_1$-$C_{12}$ alkylamido, phenyl, phenoxy, benzyl, benzyloxy, heterocyclyl or cycloalkyl;

$R_{17}$, $R_{18}$, $R_{19}$ and $R_{20}$ are each independently H, $C_1$-$C_4$alkyl, $C_3$-$C_8$cycloalkyl or and $R_{18}$ or $R_{19}$ and $R_{20}$ may be taken together with the atom to which they are attached to form a 5- to 7-membered ring optionally containing an additional heteroatom selected from O, N or S; and p is 0, 1 or 2 which process comprises reacting a compound of formula II

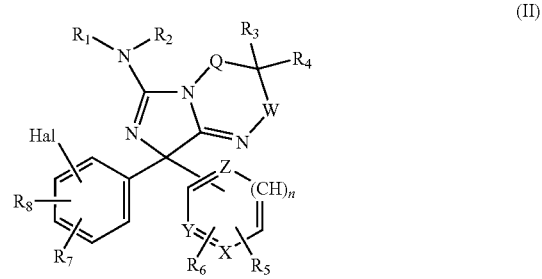

wherein Hal is Cl or Br and $R_1$, $R_2$, $R_3$, $R_4$, $R_5$, $R_6$, $R_7$, $R_8$, n, Q, W, X, Y and Z are as described for formula Ia hereinabove with an optionally substituted aryl or heteroaryl group having a leaving group selected from $B(OH)_2$, Sn(n Bu)3 or $Sn(CH_3)_3$ in the presence of a palladium catalyst optionally in the presence of a solvent.

* * * * *